(12) United States Patent
Kukkola et al.

(10) Patent No.: US 6,277,987 B1
(45) Date of Patent: *Aug. 21, 2001

(54) SULFONYLAMINO ACID AND SULFONYLAMINO HYDROXAMIC ACID DERIVATIVES

(75) Inventors: Paivi Jaana Kukkola, Whitehouse Station, NJ (US); Leslie Anne Robinson, Del Mar, CA (US); Motowo Nakajima, Ashiya; Junichi Sakaki, Takarazuka, both of (JP)

(73) Assignee: Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/243,854

(22) Filed: Feb. 3, 1999

Related U.S. Application Data
(60) Provisional application No. 60/135,514, filed on Feb. 4, 1998.

(51) Int. Cl.⁷ ............... C07D 239/72; C07D 209/48; C07D 275/04; A61K 31/415; A61K 31/40
(52) U.S. Cl. ............... 544/285; 548/477; 548/209; 548/317.1; 514/259; 514/373; 514/417; 514/389
(58) Field of Search ............... 548/477, 209, 548/317.1; 514/417, 373, 259, 389; 544/285

(56) References Cited

U.S. PATENT DOCUMENTS

| | | |
|---|---|---|
| 3,434,944 | 3/1969 | Horner et al. . |
| 5,552,419 | 9/1996 | MacPherson et al. . |
| 5,672,615 * | 9/1997 | MacPherson et al. ............... 514/357 |
| 5,753,653 | 5/1998 | Bender et al. . |
| 5,756,545 | 5/1998 | O'Brien et al. . |
| 5,872,152 | 2/1999 | Brown et al. . |
| 5,985,900 * | 11/1999 | Bender et al. ............... 514/336 |

FOREIGN PATENT DOCUMENTS

| | | |
|---|---|---|
| 64823/98 | 12/1998 | (AU) . |
| 64824/98 | 12/1998 | (AU) . |
| 197 19 428 | 11/1998 | (DE) . |
| 197 19 585 | 11/1998 | (DE) . |
| 2237052 | 11/1998 | (CA) . |
| 2237099 | 11/1998 | (CA) . |
| 95/35276 | 12/1995 | (WO) . |
| 96/00214 | 1/1996 | (WO) . |
| 96/40101 | 12/1996 | (WO) . |
| 97/19068 | 5/1997 | (WO) . |
| 97/20824 | 6/1997 | (WO) . |
| 97/27174 | 7/1997 | (WO) . |
| 97/44315 | 11/1997 | (WO) . |
| 97/45402 | 12/1997 | (WO) . |
| 98/08814 | 3/1998 | (WO) . |
| 98/08815 | 3/1998 | (WO) . |
| 98/08822 | 3/1998 | (WO) . |

(List continued on next page.)

OTHER PUBLICATIONS

Tamura Y, et al. "Highly Selective and Orally Active Inhibitors of Type IV Collangenase (MMP-0 and MMP-2): N-Sulfonylamino Acid Derivatives," J Med Chem, V41, 640–649 (1998).

Primary Examiner—Deborah C. Lambkin
(74) Attorney, Agent, or Firm—Carol Loeschorn

(57) ABSTRACT

Compounds of formula

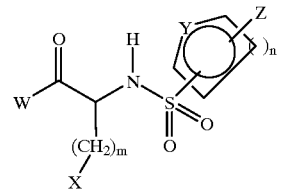

wherein
W is —OH or —NHOH;
X is a heterocycle with the proviso that when X is a nitrogen containing heterocycle, the heterocycle is attached to the $(CH_2)_m$ moiety by a ring nitrogen, $-CONR_2R_3$, $-NR_1COR_2$, $-NR_1SO_2R_2$, $-NR_1CONR_2R_3$, $-NR_1COOR_4$, heteroarylthio, alkylthio, arylalkylthio, heteroarylalkylthio, heterocycloalkylalkylthio, heterocycloalkylthio or arylthio;
Y is carbon, nitrogen, oxygen or sulfur, provided that when Y is carbon, n is 2;
Z is alkyl, aryl, alkoxy, aryloxy, aralkoxyaryl, aralkoxyheteroaryl, heteroaryl, heterocycloalkyl, heteroaryloxy, $-CONR_2R_3$, $-NR_1COR_2$, $-NR_1CONR_2R_3$, $-OCONR_2R_3$, $-NR_1COOR_4$, or $-SO_2R_2$;
$R_1$ is hydrogen, alkyl, heterocycloalkylalkyl, aralkyl or heteroarylalkyl;
$R_2$ and $R_3$ are independently $R_1$, aryl or heteroaryl; or $R_2$ and $R_3$ taken together with the nitrogen atom to which they are attached form a 5- to 7-membered ring, which may optionally contain another heteroatom selected from oxygen, nitrogen and sulfur;
$R_4$ is alkyl, heterocycloalkylalkyl, aralkyl, aryl or heteroaryl;
m represents an integer from one to six;
n represents the integer one or two; and pharmaceutically acceptable salts thereof; pharmaceutical compositions comprising said compounds; and a method of inhibiting matrix-degrading metalloproteinases in mammals using such compounds. Compounds of formula I are inhibitors of matrix-degrading metalloproteinases and are useful for the treatment of conditions related thereto.

23 Claims, No Drawings

FOREIGN PATENT DOCUMENTS

| | | |
|---|---|---|
| 98/08823 | 3/1998 | (WO) . |
| 98/08825 | 3/1998 | (WO) . |
| 98/08827 | 3/1998 | (WO) . |
| 98/08850 | 3/1998 | (WO) . |
| 98/26773 | 6/1998 | (WO) . |
| 98/31664 | 7/1998 | (WO) . |
| 98/43963 | 10/1998 | (WO) . |
| 98/50348 | 11/1998 | (WO) . |
| 99/04780 | 2/1999 | (WO) . |
| 99/06340 | 2/1999 | (WO) . |

* cited by examiner

SULFONYLAMINO ACID AND SULFONYLAMINO HYDROXAMIC ACID DERIVATIVES

CROSS REFERENCE TO RELATED APPLICATIONS

This application claims the benefit of provisional application No. 60/135,514 (converted from application Ser. No. 09/018,819) filed Feb. 4, 1998, which is incorporated herein by reference.

SUMMARY OF THE INVENTION

The invention relates to sulfonylamino acid and sulfonylamino hydroxamic acid derivatives and to processes for their preparation, pharmaceutical compositions comprising said compounds, a method of inhibiting matrix-degrading metalloproteinases in mammals using such compounds and the use of these derivatives as medicaments.

The present invention relates to novel sulfonylamino acid and sulfonylamino hydroxamic acid derivatives of formula

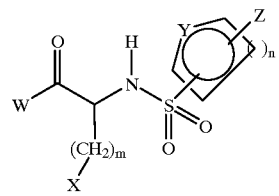

and pharmaceutically acceptable salts thereof. As used in formula I, and throughout the specification, the symbols have the following meanings:

W is —OH or —NHOH;

X is a heterocycle with the proviso that when X is a nitrogen containing heterocycle, the heterocycle is attached to the $(CH_2)_m$ moiety by a ring nitrogen, —$CONR_2R_3$, —$NR_1COR_2$, —$NR_1SO_2R_2$, —$NR_1CONR_2R_3$, —$NR_1COOR_4$, heteroarylthio, alkylthio, arylalkylthio, heteroarylalkylthio, heterocycloalkylalkylthio, heterocycloalkylthio or arylthio;

Y is carbon, nitrogen, oxygen or sulfur, provided that when Y is carbon, n is 2;

Z is alkyl, aryl, alkoxy, aryloxy, aralkoxyaryl, aralkoxyheteroaryl, heteroaryl, heterocycloalkyl, heteroaryloxy, —$CONR_2R_3$, —$NR_1COR_2$, —$NR_1CONR_2R_3$, —$OCONR_2R_3$, —$NR_1COOR_4$, or —$SO_2R_2$;

$R_1$ is hydrogen, alkyl, heterocycloalkylalkyl, aralkyl or heteroarylalkyl;

$R_2$ and $R_3$ are independently $R_1$, aryl or heteroaryl; or $R_2$ and $R_3$ taken together with the nitrogen atom to which they are attached form a 5- to 7-membered ring, which may optionally contain another heteroatom selected from oxygen, nitrogen and sulfur;

$R_4$ is alkyl, heterocycloalkylalkyl, aralkyl, aryl or heteroaryl;

m represents an integer from one to six; and n represents the integer one or two.

Preferably X is a) an unsubstituted or substituted heterocyclic radical, selected from the group consisting of pyrrolidinyl, pyrrolyl, pyrazolyl, oxetanyl, pyrazolinyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidinyl, pyridyl, pyrazinyl, pyridazinyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, benzothiazolyl, benzoxazolyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl, dihydrobenzoisothiazolyl, dihydroquinazolinyl, tetrahydro-quinazolinyl and 10 to 15 membered tricyclic ring systems, which have at least one heteroatom in at least one carbon atom-containing ring, in which each ring of the heterocyclic radical containing a heteroatom may have 1, 2 or 3 heteroatoms selected from nitrogen atoms, oxygen atoms and sulfur atoms; with the proviso that when X is a nitrogen containing heterocyclic radical, the heterocyclic radical is attached to the $(CH_2)_m$ moiety by a ring nitrogen and the proviso that nitrogen and sulfur heteroatoms of the heterocyclic radical may also be oxidized;

b) —$NR_1SO_2R_2$, in which $R_1$ is hydrogen, alkyl, heterocyclylalkyl, aralkyl or heteroarylalkyl and $R_2$ is hydrogen, alkyl, heterocyclylalkyl, aralkyl, heteroarylalkyl, aryl or heteroaryl;

c) heterocyclylalkylthio;

d) —$CONR_2R_3$, in which $R_2$ and $R_3$ taken together with the nitrogen atom to which they are attached form a 5- to 7-membered ring, which may optionally contain another heteroatom selected from oxygen, nitrogen and sulfur, or e) —$NR_1COR_2$, in which $R_1$ is hydrogen, alkyl, heterocyclylalkyl, aralkyl or heteroarylalkyl and $R_2$ is hydrogen, heterocyclylalkyl, aralkyl, heteroarylalkyl or aryl;

Y is carbon, nitrogen, oxygen or sulfur, provided that when Y is carbon, n is 2;

Z is alkyl, aryl, alkoxy, aryloxy, aralkoxyaryl, aralkoxyheteroaryl, heteroaryl, heterocyclyl, heteroaryloxy, —$CONR_2R_3$, —$NR_1COR_2$, —$NR_1CONR_2R_3$, —$OCONR_2R_3$, —$NR_1COOR_4$, or —$SO_2R_2$, in which $R_1$ is hydrogen, alkyl, heterocyclylalkyl, aralkyl or heteroarylalkyl and $R_2$ and $R_3$ are independently hydrogen, alkyl, heterocyclylalkyl, aralkyl, heteroarylalkyl, aryl or heteroaryl; or $R_2$ and $R_3$ taken together with the nitrogen atom to which they are attached form a 5- to 7-membered ring, which may optionally contain another heteroatom selected from oxygen, nitrogen and sulfur; and $R_4$ is alkyl, heterocyclylalkyl, aralkyl, aryl or heteroaryl.

Compounds of formula I are inhibitors of matrix-degrading metalloproteinases and are useful for the treatment of conditions related thereto.

DETAILED DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances either individually or as part of a larger group).

The term "alkyl" refers to optionally substituted straight or branched chain hydrocarbon groups having 1 to 8 carbon atoms, preferably 1 to 5 carbons. Exemplary unsubstituted alkyl groups include methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like. Substituted alkyl groups include said alkyl groups substituted by one or more substituents selected from halogen, alkoxy, cycloalkyl, hydroxy, amino, nitro, cyano or thiol.

The term "alkoxy" refers to any of the above alkyl groups linked to an oxygen atom.

The term "cycloalkyl" refers to saturated cyclic hydrocarbon groups containing 3 to 7 ring carbons with cyclopropyl, cyclopentyl and cyclohexyl being preferred.

The term "halogen" or "halo" refers to chlorine, bromine, iodine and fluorine.

The term "aryl" refers to monocyclic or bicyclic aromatic hydrocarbon groups having 6 to 12 carbon atoms in the ring portion, such as phenyl, naphthyl, tetrahydronaphthyl, or biphenyl groups, each of which may optionally be substituted by one to four substituents such as alkyl, halo, hydroxy, alkoxy, amino, thiol, nitro, cyano, carboxy, heterocycle and the like.

The term "aralkyl" refers to an aryl group bonded directly through an alkyl group, such as benzyl.

The term "aryloxy" refers to an aryl group linked to an oxygen atom.

The term "aralkoxy" refers to an aryl group bonded directly through an alkoxy group.

The term "arylsulfonyl" refers to aryl—$S(O)_2$—.

The term "aroyl" refers to aryl—$C(O)$—.

The term "heterocycle" or "heterocyclic radical" refers to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidinyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydrobenzoisothiazolyl, dihydroisoindolyl, dihydroquinazolinyl (such as 3,4-dihydro-4-oxoquinazolinyl), tetrahydroquinazolinyl and the like.

Exemplary tricyclic heterocyclic groups include tetrahydroimidazo[1,5-b]isoquinolinyl, carbazolyl, benzidolyl, phenanthrolinyl, acridinyl, phenanthridinyl, xanthenyl and the like.

The term "heterocycle" or "heterocyclic radical" also includes substituted heterocycle groups. Substituted heterocycle groups refer to heterocycle groups substituted with 1, 2, 3, 4 or 5 of the following:

(a) alkyl;
(b) hydroxy (or protected hydroxy);
(c) halo;
(d) oxo (i.e. =O);
(e) amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) carbamyl, alkylcarbamyl or dialkylcarbamyl;
(l) mercapto;
(m) nitro;
(n) cyano;
(o) sulfonamido, aminosulfonyl, alkyl or dialkylsulfonyl;
(p) aryl or heteroaryl;
(q) alkylcarbonyloxy;
(r) arylcarbonyloxy;
(s) arylthio;
(t) aryloxy;
(u) alkylthio;
(v) formyl;
(w) arylalkyl; or
(x) aryl substituted with alkyl, cycloalkyl, alkoxy, hydroxy, amino, alkylamino, dialkylamino or halo.

The term "heterocyclooxy" or "heterocyclyloxy" denotes a heterocyclic group bonded through an oxygen bridge.

The term "heteroaryl" refers to an aromatic heterocycle.

The term "heteroarylsulfonyl" refers to heteroaryl—$S(O)_2$—.

The term "heteroaroyl" refers to heterocyclo—$C(O)$— or heteroaryl—$C(O)$—.

The term "heterocyclyl" denotes a heterocyclic radical.

The term "heterocyclylalkyl" denotes a heterocyclic radical bonded directly through an alkyl group.

The term "heteroarylalkyl" refers to an aromatic heterocyclic radical bonded directly through an alkyl group.

Throughout the specification, groups and substituents thereof are chosen to provide stable moieties and compounds.

The compounds of the invention depending on the nature of the substituents, possess one or more asymmetric carbon atoms. The resulting diastereoisomers, enantiomers and geometric isomers are encompassed by the instant invention.

Preferred are the compounds of the invention wherein the configuration of the asymmetric carbon atom of compounds of formula I is assigned the (R)-configuration.

Further preferred are the compounds of formula I in which

W is —OH or —NHOH;
X is a nitrogen containing heterocycle;
Y is carbon and n is two;
Z is aryl, aryloxy, heteroaryl or heteroaryloxy;
m represents an integer from two to four.

Also preferred are the compounds of formula I in which

W is —OH or —NHOH;
X is one of the following:
   1,3-dioxo-1,3-dihydroisoindolyl;
   1,2,3,4-tetrahydro-1-methyl-2,4-dioxo-quinazolinyl;
   3,4,4-trimethyl-2,5-dioxoimidazolinyl;
   4-methylbenzenesulfonylamino; or
   1,1,3-trioxo-2,3-dihydrobenzoisothiazolyl;
Z is aryl, aryloxy, heteroaryl or heteroaryloxy;
m represents an integer from two to four.

Further preferred are the compounds of formula I in which W is —OH or —NHOH; X is an unsubstituted or substituted heterocyclic radical, selected from the group consisting of pyrrolidinyl, oxetanyl, pyrazolinyl, imidazolinyl, imidazolidinyl, oxazolidinyl, isoxazolinyl, thiadiazolyl, thiazolidinyl, isothiazolyl, isothiazolidinyl, furyl, tetrahydrofuryl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidinyl, pyrazinyl, pyridazinyl, tetrahydropyranyl, morpholinyl, 1,3-dioxolane, thiamorpholinyl, thiamorpholinyl sulfoxide, thiamorpholinyl sulfone, tetrahydro-isoquinolinyl, tetrahydro-1,1-dioxothienyl, quinuclidinyl, quinolinyl, isoquinolinyl, benzopyranyl, indolizinyl, benzofuryl, chromonyl, coumarinyl, benzopyranyl, cinnolinyl, quinoxalinyl, indazolyl, pyrrolopyridyl, furopyridinyl, dihydrobenzoisothiazolyl, dihydroquinazolinyl, tetrahydroquinazolinyl and 10 to 15 membered tricyclic ring systems, which have at least one heteroatom in at least one carbon atom-containing ring, in which each ring of the heterocyclic radical containing a heteroatom may have 1, 2 or 3 heteroatoms selected from nitrogen atoms, oxygen atoms and sulfur atoms; and the remaining symbols and radicals have the same meaning as given above.

Another preferred embodiment of the invention is a compound of formula I in which W is —OH or —NHOH; X is an unsubstituted or substituted heterocyclic radical, selected from the group consisting of pyrazolyl, oxetanyl, pyrazolinyl, imidazolinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, oxadiazolyl, piperazinyl, 2-oxopiperazinyl, 2-oxopiperidinyl, 2-oxoazepinyl, pyridyl, pyrazinyl, pyridazinyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, benzothiazolyl, benzoxazolyl, quinuclidinyl, quinolinyl, tetrahydroisoquinolinyl, isoquinolinyl, benzopyranyl, benzofuryl, chromonyl, coumarinyl, benzopyranyl, cinnolinyl, quinoxalinyl, indazolyl, pyrrolopyridyl, furopyridinyl, dihydrobenzoisothiazolyl, dihydroquinazolinyl, tetrahydroquinazolinyl and 10 to 15 membered tricyclic ring systems, which have at least one heteroatom in at least one carbon atom-containing ring, in which each ring of the heterocyclic radical containing a heteroatom may have 1, 2 or 3 heteroatoms selected from nitrogen atoms, oxygen atoms and sulfur atoms; and the remaining symbols and radicals have the same meaning as given above.

Further preferred are the compounds of formula I in which W is —OH or —NHOH; X is a nitrogen containing heterocyclic radical; Y is carbon and n is two; Z is aryl, aryloxy, heteroaryl or heteroaryloxy and m represents an integer from two to four.

Particularly preferred compounds of the formula I are those in which W is —OH or —NHOH; X is one of the following: 1,2,3,4-tetrahydro-1-methyl-2,4-dioxo-quinazolinyl; 3,4,4-trimethyl-2,5-dioxoimidazolinyl; 4-methylbenzenesulfonylamino; or 1,1,3-trioxo-2,3-dihydrobenzoisothiazolyl; Z is aryl, aryloxy, heteroaryl or heteroaryloxy; Y is carbon, nitrogen, oxygen or sulfur, provided that when Y is carbon, n is 2; n represents the integer one or two and m represents an integer from two to four.

Particularly preferred compounds of the formula I are those in which W is —OH and the remaining symbols and radicals have the same meaning as given above.

Another preferred embodiment of the invention is a compound of formula I in which W is —OH or —NHOH; X is —CONR$_2$R$_3$, in which R$_2$ and R$_3$ taken together with the nitrogen atom to which they are attached form a 5- to 7-membered ring, which contains oxygen as another heteroatom; Y is carbon; n is two; Z is aryl or aryloxy and m represents an integer from one to three.

Also preferred is a compound of formula I in which W is —OH; X is 1,2,3,4-tetrahydro-1-methyl-2,4-dioxo-quinazolinyl or 1,1,3-trioxo-2,3-dihydrobenzo-isothiazolyl; Y is carbon; n is two; Z is aryl or aryloxy, whereby in each case aryl is unsubstituted or substituted by halogen and m represents an integer from two to four.

Another preferred embodiment of the invention is a compound of formula I in which W is —OH or —NHOH; X is —NR$_1$COR$_2$, in which R$_1$ is hydrogen and R$_2$ is aralkyl or aryl; Y is carbon; n is two; Z is alkoxy or aryl; and m represents an integer from three to four.

Also preferred is a compound of formula I in which W is —OH or —NHOH; X is —NR$_1$SO$_2$R$_2$, in which R$_1$ is hydrogen and R$_2$ is alkyl, heterocyclylalkyl, aralkyl, heteroarylalkyl, aryl or heteroaryl; Y is carbon; n is two; Z is alkoxy or aryl; and m represents an integer from three to four.

Pharmaceutically acceptable salts of any acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methyl-ammonium salts.

Similarly acid addition salts, such as of mineral acids, organic carboxylic, and organic sulfonic acids e.g. hydrochloric acid, methanesulfonic acid, maleic acid, are possible provided a basic group, such as pyridyl, constitutes part of the structure.

Compounds of formula I where X is a heterocycle, heteroarylthio, alkylthio, arylalkylthio, heteroarylalkylthio, heterocycloalkylalkylthio, heterocycloalkylthio or arylthio, may be prepared from N-(diphenylmethylene)glycine t-butyl ester (commercially available) and compounds of formula II

where Y is a leaving group such as a halide such as chloride, bromide or iodide; or a sulfonate such as methenesulfonate, trifluoromethanesulfonate or methylbenzenesulfonate (prepared as described in the literature); by treatment with a base such as sodium or potassium hydride in a organic solvent such as tetrahydrofuran and N,N-dimethylformamide to form compounds of formula III

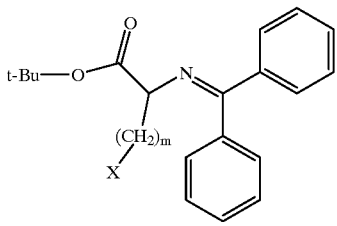

Compounds of formula III can be converted to compounds of formula IV

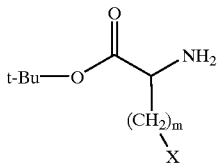

by treatment with a mild acid such as 4-methylbenzenesulfonic acid in a organic solvent such as acetonitrile and tetrahydrofuran in a presence of a small amount of water.

Sulfonylation of compounds of formula IV with sulfonyl chlorides such as 4'-chlorobiphenyl-4-sulfonyl chloride or a compound of formula V

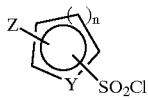

produces compounds of formula VI

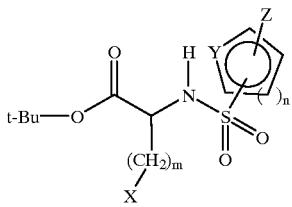

The sulfonylation can be carried out in the presence of a base such as triethylamine or N-methylmorpholine in a organic solvent such as dichloromethane, tetrahydrofuran, acetonitrile or N,N-dimethylformamide. Sulfonylchlorides of formula V can be obtained as described in the art.

Compounds of formula VI can be converted to compounds of formula I where W is a hydroxyl group by treatment with anhydrous acid such as trifluoroacetic acid or hydrochloric acid in a organic solvent such as dichloromethane, diethyl ether or ethyl acetate. The reaction can be carried out without solvent when trifluoroacetic acid is used.

Compounds of formula I where W is —NHOH can be obtained from compounds of formula I where W is a hydroxyl group via a reaction with protected hydroxylamines such as trityl-, allyl- or t-butylhydroxylamine. The reactions can be carried out in the presence of a coupling agent such as 1-hydroxy-7-azabenzotriazole and 1-(3-dimethylaminopropyl)-3-ethylcarbodiimide and a base such as triethylamine or N-methylmopholine in a organic solvent such as dichloromethane, tetrahydrofuran, acetonitrile or N,N-dimethylformamide. The protecting groups can be removed as described in the art.

Alternatively, compounds of formula I where X is a heterocycle, heteroarylthio, alkylthio, arylalkylthio, heteroarylalkylthio, heterocycloalkylalkylthio, heterocycloalkylthio or arylthio and m is 2 or 3 can be obtained from compounds of formula VII

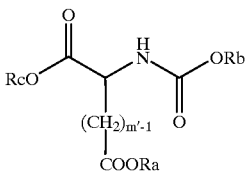

where m' is an integer of 2 or 3 and Ra, Rb and Rc are independently suitable protecting groups. For example, when Ra is methyl or ethyl and Rb and Rc are e.g. t-butyl, compounds of formula VII can be treated with a base such as lithium hydroxide, sodium hydroxide or potassium hydroxide in an aqueous solution of a organic solvent such as tetrahydrofuran, dioxane, methanol or ethanol to form compounds of formula VIII

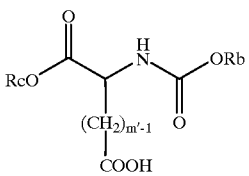

Compounds of formula VIII are then treated with alkyl chloroformate such as ethylchloroformate or isobutylchloroformate in a presence of a base such as N-methylmorpholine or triethylamine in organic solvents such as tetrahydrofuran, dioxane or ethylene glycol dimethyl ether followed by reduction using sodium borohydride to provide compounds of formula IX

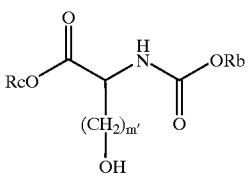

Compounds of formula IX are converted to compounds of formula X

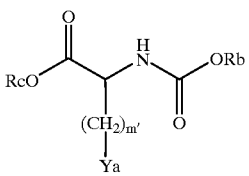

where Ya is a leaving group such as a halide, such as iodide, bromide or chloride or a sulfonate such as methanesulfonate, trifluoromethanesulfonate or 4-methylbenzenesylfonate using standard literature procedures.

Compounds of formula X are then treated with a compound (X'), where X' is a heterocycle such as phthalimide, saccharin, 1,2,3,4-tetrahydro-1-methyl-2,4-dioxoquinazoline or 3,4,4-trimethyl-2,5-dioxoimidazolidine; or heteroarylthiol, alkylthiol, arylalkylthiol, heteroarylalkylthiol, heterocycloalkylalkylthiol, heterocycloalkylthiol or arylthiol; in the presence of a base such as sodium hydride, potassium hydride, potassium carbonate or cesium carbonate in a organic solvent such as N,N-dimethylformamide to form compounds of formula XI

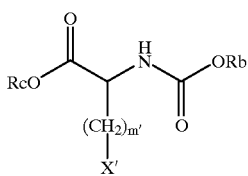

Compounds of formula XI are then selectively deprotected at the nitrogen atom using procedures known in the art to form compounds of formula XII

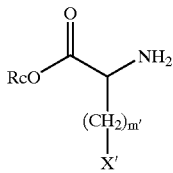

For example, where Rb and Rc are t-butyl, deprotection can be carried out by treatment with an anhydrous acid such as trifluoroacetic acid in an organic solvent such as dichloromethane.

Compounds of formula XII are then sulfonylated with sulfonyl chlorides of formula V such as 4'-chlorobiphenyl-4-sulfonyl chloride. The sulfonylation can be carried out using base such as triethylamine or N-methylmorpholine in a organic solvent such as dichloromethane, tetrahydrofuran, acetonitrile or N,N-dimethylformamide to form compounds of formula XIII

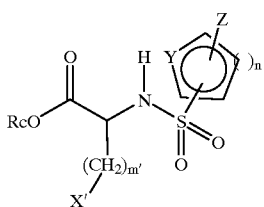

Compounds of formula XIII are converted to compounds of formula IA

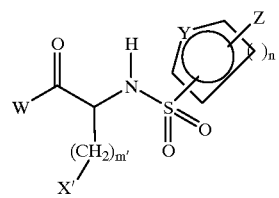

where W is OH by removal of the carboxyl protecting group using known methods. For example, where Rc is a t-butyl group, deprotection can be carried out by treatment with an anhydrous acid such as trifluoroacetic acid or hydrochloric acid in an organic solvent such as dichloromethane, diethyl ether or ethyl acetate. The reactions can be carried out without solvent when trifluoroacetic acid is used.

Compounds of formula IA where W is —NHOH can be obtained from compounds of formula IA where W is a hydroxyl group via a reaction with protected hydroxylamines such as trityl-, allyl- or t-butylhydroxylamine. The reactions can be carried out in the presence of a coupling agent such as 1-hydroxy-7-azabenzotriazole and 1-(3-dimethylaminopropyl)-3-ethylcarbodiimide and a base such as triethylamine or N-methylmopholine in a organic solvent such as dichloromethane, tetrahydrofuran, acetonitrile or N,N-dimethylformamide. The protecting groups can be removed as described in the art.

Compounds of formula VII can be prepared by methods disclosed in the literature (Schoenfelder, A.: Mann, A., Synth. Commun., 20, 2585–8 (1990)).

Compounds of formula I where m equals 1 or 2 and X is —CONR$_2$R$_3$, can be prepared from compounds of formula VIII using procedures known in the art or by modification of the procedures described herein.

Compounds of formula I when m equals 3 or 4 and X is —NH—SO$_2$—R$_2$, —NH—CO—R$_2$, —NH—CO—OR$_4$ or —NH—CO—NR$_2$R$_3$, can be prepared from compounds of formula XV

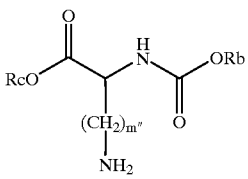

where m" is an integer of 3 or 4 (commercially available or known in the literature), using procedures known in the art or by modification of the procedures described herein.

Compounds of formula I where m equals 1 and X is alkylthio, arylalkylthio, heteroarylalkylthio, heterocycloalkylalkylthio, heterocycloalkylthio, heteroarylthio or arylthio can also be prepared from compounds of formula XVI

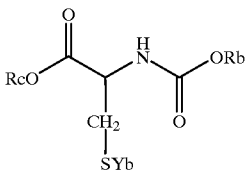

where Yb is a protecting group such as an acyl or can form a disulfide dimer, (commercially available or known in the literature), using procedures known in the art or by modification of the procedures described herein.

Other compounds of formula I may be prepared by modification of the procedures and examples described herein.

The starting compounds and intermediates which are converted to the compounds of the invention in a manner described herein, functional groups present, such as amino, thiol, carboxyl, and hydroxy groups, are optionally protected by conventional protecting groups that are common in preparative organic chemistry. Protected amino, thiol, carboxyl, and hydroxy groups are those that can be converted under mild conditions into free amino, thiol, carboxyl and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1991.

In the processes cited herein, reactive functional derivatives of carboxylic acids represent, for example, anhydrides (especially mixed anhydrides), acid halides, acid azides, lower alkyl esters, and activated esters thereof. Mixed anhydrides are preferably such from pivalic acid, or a lower alkyl (ethyl, isobutyl) hemiester of carbonic acid; acid halides are for example chlorides or bromides; activated esters for example succinimido, phthalimido or 4-nitrophenyl esters; lower alkyl esters are for example the methyl or ethyl esters.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials and processes for their manufacture.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The carboxylic acid intermediates can thus be resolved into their optical antipodes e.g. by fractional crystallization of d- or 1-(alpha-methylbenzylamine, cinchonidine, cinchonine, quinine, quinidine, ephedrine, dehydroabietylamine, brucine or strychnine)-salts. Racemic products can also be resolved by chiral chromatography, e.g. high pressure liquid chromatography using a chiral adsorbent.

Finally, compounds of the invention are either obtained in the free form, or as a salt thereof if salt forming groups are present.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$)-alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$–$C_4$)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit matrix-degrading metalloproteinases, and for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g. to the skin and eyes, are preferably aqueous solutions, ointments, creams or gels well-known in the art.

The pharmaceutical formulations contain an effective matrix-degrading metalloproteinase inhibiting amount of a compound of the invention as defined above, either alone or in combination with another therapeutic agent, e.g. an antiinflammatory agent with cyclooxygenase inhibiting activity, or other antirheumatic agents such as methotrexate, each at an effective therapeutic dose as reported in the art. Such therapeutic agents are well-known in the art.

Examples of antiinflammatory agents with cyclooxygenase inhibiting activity are diclofenac, naproxen, ibuprofen, and the like.

In conjunction with another active ingredient, a compound of the invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 10 and 1000 mg, advantageously between about 25 and 500 mg of the active ingredient.

The compounds of the invention inhibit matrix degrading metalloproteinase such as gelatinase, stromelysin, collagenase, (including collagenase 1 and 3), and macrophage metalloelastase, and membrane type matrix metalloproteinases, such as MT-MMP 1 and 2. They are particularly useful as collagenase-3 inhibitors.

Thus the compounds of the invention inhibit matrix degradation and are useful for the treatment of gelatinase-, stromelysin-, collagenase-, and macrophage metalloelastase-dependent pathological conditions in mammals. Such conditions include malignant and non-malignant tumors (by inhibiting tumor growth, tumor metastasis, tumor progression or invasion and/or tumor angiogenesis), such tumors including e.g. breast, lung, bladder, colon, ovarian, and skin cancer. Other conditions to be treated with the compounds of the invention include rheumatoid arthritis osteoarthritis, bronchial disorders (such as asthma by inhibiting the degradation of elastin), atherosclerotic conditions (by e.g. inhibiting rupture of atherosclerotic plaques), as well as acute coronary syndrome, heart attacks (cardiac ischemia), strokes (cerebral ischemias), restenosis after angioplasty, and also vascular ulcerations, ectasia and aneurysms.

Further conditions to be treated with the compounds of the invention are inflammatory demyelinating disorders of the nervous system in which myelin destruction or loss is involved (such as multiple sclerosis), optic neuritis, neuromyelitis optica (Devic's disease), diffuse and transitional sclerosis (Schilder's disease) and acute disseminated encephalomyelitis, also demyelinating peripheral neuropathies such as Landry-Guillain-Barre-Strohl syndrome for motor defects; also tissue ulceration (e.g. epidermal and gastric ulceration), abnormal wound healing, periodental disease, bone disease (e.g. Paget's disease and osteoporosis). Also endometriosis, septic shock, inflammatory bowel disease, Crohn's disease and the like.

Ocular applications of the compounds of the invention include the treatment of ocular inflammation, corneal ulcerations, pterygium, keratitis, keratoconus, open angle glaucoma, retinopathies, and also their use in conjunction with refractive surgery (laser or incisional) to minimize adverse effects.

The compounds are particularly useful for the treatment of e.g. inflammatory conditions, osteoarthritis, rheumatoid arthritis and tumors.

Beneficial effects are evaluated in pharmacological tests generally known in the art, and as illustrated herein.

The above-cited properties are demonstrable in in vitro and in vivo tests, using advantageously mammals, e.g. rats, guinea pigs, dogs, rabbits, or isolated organs and tissues, as well as mammalian enzyme preparations. Said compounds can be applied in vitro in the form of solutions, e.g. preferably aqueous solutions, and in vivo either enterally or parenterally, advantageously orally, e.g. as a suspension or in aqueous solution. The dosage in vitro may range between about $10^{-5}$ molar and $10^{-10}$ molar concentrations. The dosage in vivo may range, depending on the route of administration, between about 0.1 and 100 mg/kg.

Antiinflammatory activity can be determined in standard inflammation and arthritic animal models well-known in the art, e.g. the adjuvant arthritis model in rats and the collagen II induced arthritis model in mice (Mediators of Inflam. 1, 273–279 (1992).

One test to determine the inhibition of stromelysin activity is based on its hydrolysis of Substance P using a modified procedure of Harrison et al (Harrison, R. A., Teahan J., and Stein R., A semicontinuous, high performance chromatography based assay for stromelysin, Anal. Biochem. 180, 110–113 (1989)). In this assay, Substance P is hydrolyzed by recombinant human stromelysin to generate a fragment, Substance P 7-11, which can be quantitated by HPLC. In a typical assay, a 10 mM stock solution of a compound to be tested is diluted in the assay buffer to 50 mM, mixed 1:1 with 8 mg recombinant human stromelysin (mol. wt. 45–47 kDa, 2 Units; where 1 Unit produces 20 mmoles of Substance P 7-11 in 30 minutes) and incubated along with 0.5 mM Substance P in a final volume of 0.125 mL for 30 minutes at 37° C. The reaction is stopped by adding 10 mM EDTA and Substance P 7-11 is quantified on RP-8 HPLC. The $IC_{50}$ for inhibition of stromelysin activity and Ki are calculated from control reaction without the inhibitor.

Illustrative of the invention the compound of Example 1 exhibits an $IC_{50}$ of about 130 nM in this assay.

Stromelysin activity can also be determined using human aggrecan as a substrate. This assay allows the confirmation in-vitro that a compound can inhibit the action of stromelysin on its highly negatively-charged natural substrate, aggrecan (large aggregating prtoeoglycan). Within the cartilage, proteoglycan exists as an aggregate bound to hyaluronate. Human proteoglycan aggregated to hyaluronate is used as an enzyme substrate. The assay is set up in 96-well microtiter plates allowing rapid evaluation of compounds. The assay has three major steps:
1) Plates are coated with hyaluronate (human umbilical chord, 400 ug/mL), blocked with BSA (5 mg/mL), and then proteoglycan (human articular cartilage D1—chondroitinase ABC digested, 2 mg/mL) is bound to the hyaluronate. Plates are washed between each step.
2) Buffers+inhibitor (1 to 5,000 nM)+recombinant human stromelysin (1–3 Units/well) are added to wells. The plates are sealed with tape and incubated overnight at 37° C. The plates are then washed.
3) A primary (3B3) antibody (mouse IgM, 1:10,000) is used to detect remaining fragments. A secondary antibody, peroxidase-linked anti-IgM, is bound to the primary antibody. OPD is then added as a substrate for the peroxidase and the reaction is stopped with sulfuric acid. The $IC_{50}$ for inhibition of stromelysin activity is graphically derived and Ki is calculated.

Collagenase-1 inhibitory activity is determined as follows: ninety six-well, flat-bottom microtiter plates are first coated with bovine type I collagen (35 ug/well) over a two-day period at 30° C. using a humidified and then dry atmosphere; plates are rinsed, air dried for 3–4 hours, sealed with Saran wrap and stored in a refrigerator. Human recombinant fibroblast collagenase and a test compound (or buffer) are added to wells (total volume=0.1 mL) and plates are incubated for 2 hours at 35° C. under humidified conditions; the amount of collagenase used per well is that causing approximately 80% of maximal digestion of collagen. The incubation media are removed from the wells, which are then rinsed with buffer, followed by water. Coomasie blue stain is added to the wells for 25 minutes, removed, and wells are again rinsed with water. Sodium dodecyl sulfate (20% in 50% dimethylformamide in water) is added to solubilize the remaining stained collagen and the optical density at 570 nM wave length is measured. The decrease in optical density due to collagenase (from that of collagen without enzyme) is compared to the decrease in optical density due to the enzyme in the presence of test compound, and percent inhibition of enzyme activity is calculated. $IC_{50}$'s are determined from a range of concentrations of inhibitors (4–5 concentrations, each tested in triplicate), and $K_i$ values are calculated.

Illustrative of the invention, the compound of Example 2 exhibits an $IC_{50}$ of about 75 nM.

Collagenase-3 inhibitory activity is determined as follows: One nM stock solutions of substrate (MCA-Pro-Leu-Gly-Dpa-Ala-Arg-$NH_2$, J. Biol. Chem. 271, 1544–1550, 1996) and 10 nM stock solution of inhibitor are prepared in DMSO. They are diluted with assay buffer (20 nM tris at pH 7.5 containing 10 mM $CaCl_2$, 0.002% sodium azide) as needed. Recombinant pro-collagenase-3 is activated with 1 mM APMA, and stored in the assay buffer after extensive dialysis in the assay buffer. Recombinant enzyme solution (0.05 mL, 1.3 nM) is mixed with 0.05 mL of inhibitor solution at various concentrations for 10 minutes at room temperature. Then 0.025 mL of 8 $\mu$M substrate solution is added and fluorescence ($\lambda$ex=325; $\lambda$em=405) is continuously measured at room temperature. The percent inhibition of collagenase-3 activity is determined from the effect of inhibitor at various concentrations on the change in fluorescence; the $IC_{50}$ is determined graphically.

Illustrative of the invention, the compound of Example 1 exhibits an $IC_{50}$ of about 4 nM.

The effect of compounds of the invention in-vivo can be determined in rabbits. Typically, four rabbits are dosed orally with a compound up to four hours before being injected intra-articularly in both knees (N=8) with 40 Units of recombinant human stromelysin dissolved in 20 mM Tris, 10 mM $CaCl_2$, and 0.15 M NaCl at pH 7.5. Two hours later the rabbits are sacrificed, synovial lavage is collected, and keratan sulfate (KS) and sulfated glycosaminoglycan (S-GAG) fragments released into the joint are quantitated. Keratan sulfate is measured by an inhibition ELISA using the method of Thonar (Thonar, E. J. -M. A., Lenz, M. E., Klinsworth, G. K., Caterson, B., Pachman, L. M., Glickman, P., Katz, R., Huff, J., Keuttner, K. E. Quantitation of keratan sulfate in blood as a marker of cartilage catabolism, Arthr. Rheum. 28, 1367–1376 (1985)). Sulfated glycosaminoglycans are measured by first digesting the synovial lavage with streptomyces hyaluronidase and then measuring DMB dye binding using the method of Goldberg (Goldberg, R. L. and Kolibas, L. An improved method for determining proteoglycan synthesized by chondrocytes in culture. Connect. Tiss. Res. 24, 265–275 (1990)). For an i.v. study, a compound is solubilized in 1 mL of PEG-400, and for a p.o. study, a compound is administered in 5 mL of fortified corn starch per kilogram of body weight.

The effect in protecting against cartilage degradation in arthritic disorders can be determined e.g. in a surgical model of osteoarthritis described in Arthritis and Rheumatism, Vol. 26, 875–886 (1983).

The effect on ulcerations, e.g. ocular ulcerations, can be determined in the rabbit by measuring the reduction of corneal ulceration following an alkali burn to the cornea.

Macrophage metalloelastase (MME) inhibitory activity can be determined by measuring the inhibition of the degradation of [$^3$H]-elastin by truncated recombinant mouse macrophage metalloelastase as follows:

About 2 ng of recombinant truncated mouse macrophage metalloelastase (FASEB Journal Vol. 8, A151, 1994), purified by Q-Sepharose column chromatography is incubated with test compounds at the desired concentrations in the presence of 5 nM $CaCl_2$, 400 nM NaCl, [$^3$H]elastin (60,000 cpm/tube), and 20 mM Tris, pH 8.0, at 37° C. overnight. The samples are spun in a microfuge centrifuge at 12,000 rpm for 15 minutes. An aliquot of the supernatant is counted in a scintillation counter to quantitate degraded [$^3$H]elastin. $IC_{50}$'s are determined from a range of concentrations of the test compounds and the percent inhibition of enzyme activity obtained.

The effect of the compounds of the invention for the treatment of emphysema can be determined in animal models described in American Review of Respiratory Disease 117, 1109 (1978).

The antitumor effect of the compounds of the invention can be determined e.g. by measuring the growth of human tumors implanted subcutaneously in Balb/c nude treated mice according to methodology well-known in the art in comparison to placebo treated mice. Illustrative tumors are e.g. estrogen dependent human breast carcinoma BT20 and MCF7, human bladder carcinoma T24, human colon carcinoma Colo 205, human lung adenocarcinoma A549 and human ovarian carcinoma NIH-OVCAR3.

The effect on tumor angiogenesis can be determined e.g. in rats implanted with Walker 256 carcinoma in pellets to stimulate angiogenesis from vessels of the limbus, as described by Galardy et al, Cancer Res. 54, 4715 (1994).

Gelatinase A and MT1-MMP inhibitory activities can be determined as follows: Stock solutions of substrate (MCA- Pro-Leu-Gly-Leu-Dpa-Ala-Arg-NH$_2$, Knight, C. G., Willenbrock, F., Murphy, G., A novel coumarin-labelled peptide for sensitive continous assays of the matrix metalloproteinases, FEBS lett., 296, 263–266, (1992)), are prepared in 100% DMSO at a concentration 1.0 mM. Stock solutions of inhibitors are prepared in 100% DMSO. The inhibitor is diluted into the assays from a solution in 100% DMSO, and controls substitute an equal volume of DMSO so that the final DMSO concentration from inhibitor and substrate dilutions in all assays is 6.0%. Assays are performed in assay buffer (150 mM NaCl, 10 mM CaCl$_2$, 50 mM Tris-Cl pH7.5, 0.05% Brij-35) containing 6.0% DMSO once the substrate and inhibitor are diluted into it. The substrate concentration used in the assays is 10 $\mu$M. The test is carried out at 37° C. The fluorescence changes are monitored using an excitation wavelength of 320 nm and an emission wavelength of 340 nm. The reaction mixture is added in duplicate to appropriate wells of a 96 well microfluor plate. The reaction mixture is preincubated with the inhibitor for 30 min, the reaction is started by the addition of MMP enzyme and the fluorescence intensity is measured for 10 min. A time point that is on a linear part of the curve is chosen to determine the activity. The inhibition results are expressed as the inhibitor concentrations that produced 50% inhibition (IC$_{50}$) of the activity in the control (non-inhibited) reaction.

The inhibition of tumor metastasis can be determined in two lung metastasis models: In the B16-F10 melanoma model metastasis is measured by counting the numbers of lung metastasized melanoma nodules produced by intravenously injected B16-F10 melanoma cells into BDF1 treated mice according to methodology well known in the art. In the HT1080 model and metastasis is quantified by measuring the fluorescence intensity of enhanced green fluorescent protein (EGFP) in the lung of Balb/c nude mice produced by the meta-stasized tumor from intravenously injected GFP-expressing human fibrosarcoma HT1080 cells. The inhibition is obtained by comparison of compound treated and placebo treated mice in both methods. In HT1080 model, EGFP expressing HT1080 cell is prepared by limiting dilution method in the presence of geneticin after transfecting the EGFP expression vector (pEGFP-Cl) (CLONTECH Laboratories Inc., Palo Alto, Calif.). A suspension of cells (10$^6$ cells/0.1 mL of PBS) is injected intravenously in Balb/c nude mice. After administering test compounds and vehicle p.o. 3 weeks, tumor metastasized lung of mice are removed after sacrifice and homogenized. After centrifugation, the cells are washed 3 times with lysing reagent (150 mM NH$_4$Cl, 0.1 mM EDTA-4 Na, 10 mM KHCO$_3$, pH 7.4) to lysis red blood cells and 2 times with PBS. After centrifugation, EGFP is extracted from cells by 10% Triton in PBS and poured into the wells of 96-well multi plate. The fluorescence intensity is determined by use of a fluorescence plate reader at the excitation and emission wave length of 485 and 530 nm, respectively.

The effect of the compounds of the invention on atherosclerotic conditions can be evaluated using atherosclerotic plaques from cholesterol-fed rabbits which contain activated matrix metalloproteinases as described by Sukhova et al, Circulation 90, I 404 (1994). The inhibitory effect on matrix metalloproteinase enzyme activity in rabbit atherosclerotic plaques can be determined by in situ zymography, as described by Galis et al, J. Clin. Invest. 94, 2493 (1994), and is indicative of plaque rupture.

The effect on vascular aneurysms, e.g. the inhibition of aneurysm formation, can be determined in experimental models such as Apo-E transgenic mice and/or LDL receptor knockout mice.

The effect on restenosis and vascular remodeling can be evaluated in the rat ballooned carotid artery model.

The effect on demyelinating disorders of the nervous system, such as multiple sclerosis, can be evaluated by measuring the reversal of experimental autoimmune encephalomyelitis in mice, e.g. as described by Gijbels et al, J. Clin. Invest. 94, 2177 (1994).

The compounds of the invention are particularly useful in mammals as antiinflammatory agents for the treatment of e.g. osteoarthritis, rheumatoid arthritis, and as antitumor agents for the treatment and prevention of tumors growth, tumor metastasis, tumor invasion or progression and as antiatherosclerotic agents for the treatment and prevention of the rupture of atherosclerotic plaques.

The present invention also relates to methods of using the compounds of the invention and their pharmaceutically acceptable salts, or pharmaceutical compositions thereof, in mammals for inhibiting the matrix-degrading metalloproteinases, e.g. stromelysin, gelatinase, collagenase and macrophage metalloelastase, for inhibiting tissue matrix degradation, and for the treatment of matrix-degrading metalloproteinase dependent conditions as described herein, e.g. inflammation, rheumatoid arthritis, osteoarthritis, also tumors (tumor growth, metastasis, progression or invasion), pulmonary disorders, and the like described herein. Tumors (carcinomas) include mammalian breast, lung, bladder, colon, prostate and ovarian cancer, and skin cancer, including melanoma and Kaposi's sarcoma.

The following Examples are intended to illustrate the invention and are not to be construed as being limitations thereon. Temperatures are given in degrees Centigrade. If not mentioned otherwise, all evaporations are performed under reduced pressure, preferably between about 15 and 100 mmHg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art. The concentration for [a]$_D$ determinations is expressed in mg/mL.

EXAMPLE 1

(2R)-(4'-Chlorobiphenyl-4-sulfonylamino)-5-(1,3-dioxo-1,3-dihydroisoindol-2-yl)pentanoic acid

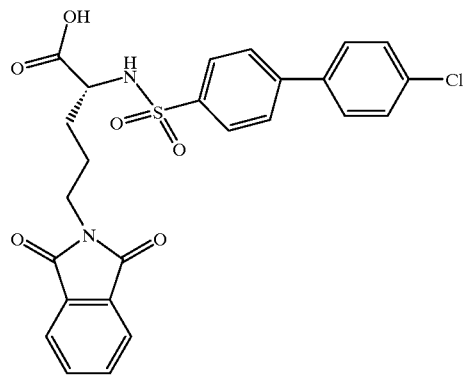

A. D-Glutamic acid γ-methyl ester hydrochloride

Thionyl chloride (34.0 mL, 468 mmol) is added dropwise over 50 min to 230 mL of methanol at −10° C., and D-glutamic acid (50.0 g, 340 mmol) is added in portions over 20 min to give a white slurry which is allowed to warm to 10° C. over 30 min. The clear solution is slowly poured into 330 mL of diethyl ether to precipitate a white solid which is collected by vacuum filtration, washed with three 60 mL portions of diethyl ether and dried to give 47.4 g (71%) of D-glutamic acid γ-methyl ester hydrochloride as a white solid: NMR(DMSO-$d_6$) 1.95–2.13 (m, 2H), 2.41–2.63 (m, 2H), 3.60 (s, 3H), 3.90 (m, 1H), 8.48 (br s, 3H); IR 1736, 1720; ESI-MS 160 ($M^-$–1).

B. D-N-(t-Butyloxycarbonyl)glutamic acid γ-methyl ester

A slurry of the title A compound, D-glutamic acid γ-methyl ester hydrochloride (47.4 g, 240 mmol) in 800 mL of tetrahydrofuran (THF) is treated with triethylamine (99.0 mL, 710 mmol) at 0° C. over 20 min, and to the cold mixture is added portionwise di-t-butyl dicarbonate (54.5 g, 250 mmol) over 40 min. The reaction is warmed slowly to room temperature (RT) and after 16 h, the mixture is concentrated, and the residue is partitioned between 800 mL of ethyl acetate and 240 mL of cold 2N aqueous hydrochloric acid HCl). The organic solution is washed with two 200 mL portions of cold water, dried over anhydrous magnesium sulfate ($MgSO_4$) and concentrated to give 59.1 g (94%) of D-N-(t-butyloxycarbonyl)glutamic acid γ-methyl ester as a colorless oil: NMR($CDCl_3$) 1.43 (s, 9H), 1.95–2.05 (m, 1H), 2.16–2.28 (m, 1H), 2.42–2.53 (m, 2H), 3.670 (s, 3H), 4.30–4.38 (m, 1H), 5.19 (br d, 1H, J=7.0).

C. D-N-(t-Butyloxycarbonyl)glutamic acid α-t-butyl, γ-methyl ester

A solution of the title B compound, D-N-(t-butyloxycarbonyl)glutamic acid γ-methyl ester (24.3 g, 93.1 mmol) in 200 mL of toluene at 80° C. is treated dropwise over 3 h with N,N-dimethylformamide di-t-butyl acetal (25.0 g, 122.9 mmol). After an additional 2 h at 80° C., the solution is cooled and concentrated, and the residue is partitioned between 400 mL of ethyl acetate and 200 mL of water. The organic solution is washed with two 100 mL portions of 1M aqueous sodium bicarbonate ($NaHCO_3$) and 100 mL of water, dried over anhydrous $MgSO_4$ and concentrated. Chomatography on silica gel (eluant; 3/7—ethyl acetate/hexane) affords 10.1 g (34%) of D-N-(t-butyloxycarbonyl)glutamic acid α-t-butyl, γ-methyl ester as a colorless oil: NMR($CDCl_3$) 1.42 (s, 9H), 1.45 (s, 9H), 1.86–1.97 (m, 1H), 2.10–2.21 (m, 1H), 2.30–2.50 (m, 2H), 3.66 (s, 3H), 4.17–4.25 (m, 1H), 5.06 (br d, 1H, J=7.6).

D. D-N-(t-Butyloxycarbonyl)glutamic acid α-t-butyl ester

A solution of the title C compound, D-N-(t-butyloxycarbonyl)glutamic acid α-t-butyl, γ-methyl ester (10.3 g, 32.8 mmol) in 100 mL of methanol at RT is treated in one portion with 1M aqueous lithium hydroxide (35.0 mL, 35.0 mmol). After stirring for 1 h, 1M aqueous HCl is added to precipitate a white, waxy solid which is extracted into 200 mL of ethyl acetate. The organic solution is dried over anhydrous $MgSO_4$ and concentrated under reduced pressure to give 9.72 g (99%) of D-N-(t-butyloxycarbonyl) glutamic acid α-t-butyl ester as white solid: NMR($CDCl_3$) 1.42 (s, 9H), 1.45 (s, 9H), 1.85–1.95 (m, 1H), 2.10–2.24 (m, 1H), 2.36–2.52 (m, 2H), 4.19–4.27 (m, 1H), 5.17 (br d, 1H, J=7.7); ESI-MS 302 ($M^-$–1).

E. (2R)-(t-Butyloxycarbonylamino)-5-hydroxypentanoic acid t-butyl ester

A solution of the title D compound, D-N-(t-butyloxycarbonyl)glutamic acid α-t-butyl ester (9.72 g, 32.0 mmol) and N-methylmorpholine (NMM) (3.70 mL, 33.6 mmol) in 50 mL of THF at –15° C. is treated dropwise over 15 min with ethyl chloroformate (3.37 mL, 35.2 mmol). After 10 min, N-methylmorpholine hydrochloride is removed by filtration, the filtrate is cooled to –40° C., and a solution of sodium borohydride (1.99 g, 52.5 mmol) in 20 mL of water is added dropwise over 15 min. The reaction mixture is allowed to warm to RT over 1 h, and is then partitioned between 200 mL of ethyl acetate and 200 mL of 1M aqueous $NaHCO_3$. The organic solution is washed with 200 mL of 1M aqueous sodium hydroxide (NaOH) and 50 mL of aqueous saturated $NaHCO_3$, dried over anhydrous sodium sulfate ($Na_2SO_4$) and concentrated. Chomatography on silica gel (eluant; 3/7—ethyl acetate/hexane) affords 9.12 g (98%) of (2R)-(t-butyloxycarbonylamino)-5-hydroxypentanoic acid t-butyl ester as a colorless oil: NMR ($CDCl_3$) 1.42 (s, 9H), 1.44 (s, 9H), 1.55–1.92 (m, 4H), 3.66 (t, 2H, J=5.7), 4.19–4.27 (m, 1H), 5.15 (br d, 1H, J=7.4); ESI-MS 290 ($M^+$+1).

F. (2R)-(t-Butyloxycarbonylamino)-5-iodopentanoic acid t-butyl ester

A solution of the title E compound, (2R)-(t-butyloxycarbonylamino)-5-hydroxypentanoic acid t-butyl ester (9.12 g, 31.5 mmol), imidazole (3.22 g, 47.3 mmol) and triphenylphosphine (12.40 g, 47.3 mmol) in 300 mL of THF is treated portionwise over 5 min with iodine (9.60 g, 37.8 mmol) at RT. After 2 h, the mixture is filtered and concentrated. The residue is first filtrated though silica gel (eluant; ethyl acetate) then purified by chomatography on silica gel (eluant; 10% ethyl acetate in hexane) affording 9.05 g (72%) of (2R)-(t-butyloxycarbonylamino)-5-iodopentanoic acid t-butyl ester as a colorless oil: NMR ($CDCl_3$)) 1.42 (s, 9H), 1.46 (s, 9H), 1.65–1.95 (m, 4H), 3.14–3.28 (m, 2H), 4.19–4.26 (m, 1H), 5.06 (br d, 1H, J=7.4); IR 1712, 1500, 1155; ESI-MS 400 ($M^+$+1).

G. (2R)-(t-Butyloycarbonylamino)-5-(1,3-dioxo-1,3-dihydroisoindol-2-yl)pentanoic acid t-butyl ester Sodium hydride (0.522 g, 13.05 mmol) is added to a solution of phthalimide (2.33 g, 15.84 mmol) and 18-crown-6 (0.01 g) in 20 mL of N,N-dimethylformamide (DMF). After stirring at RT for 20 min, a solution of the title F compound, (2R)-(t-butyloxycarbonylamino)-5-iodopentanoic acid t-butyl ester (4.61 g, 11.55 mmol) in 5 mL of DMF is added, and the solution is stirred at RT for 30 min, then at 60° C. for 8 h. The solvent is removed under reduced pressure, and the residue is partitioned between 300 mL of ethyl acetate and 225 mL of 0.05M aqueous HCl. The organic phase is washed with 100 mL water and 50 mL of brine, dried over anhydrous $Na_2SO_4$ and concentrated to give 4.83 g (100%) of (2R)-(t-butyloxycarbonylamino)-5-(1,3-dioxo-1,3-dihydroisoindol-2-yl)pentanoic acid t-butyl ester as a tan solid: NMR($CDCl_3$) 1.43 (s, 9H), 1.45 (s, 9H), 1.60–1.88 (m, 4H), 3.71 (t, 2H, J=6.6), 4.18–4.26 (m, 1H), 5.06 (br d, 1H, J=7.9), 7.70–7.73 (m, 2H), 7.83–7.86 (m, 2H); IR 1712, 1500, 1155; ESI-MS 290 ($M^+$+1).

H. (2R)-Amino-5-(1,3-dioxo-1,3-dihydroisoindol-2-yl) pentanoic acid t-butyl ester A solution of the title G compound, (2R)-(t-butyloxycarbonylamino)-5-(1,3-dioxo-1,3-dihydroisoindol-2-yl)pentanoic acid t-butyl ester (4.83 g, 11.55 mmol) in 18 mL of dichloromethane is treated with trifluoroacetic acid (TFA; 6.00 mL, 78 mmol) at 0° C. After stirring for 1 h at this temperature, the solution is concentrated under reduced pressure without heating, and the residue is partitioned between 100 mL of ethyl acetate and 50 mL of 1M aqueous $NaHCO_3$. The organic phase is dried over anhydrous $Na_2SO_4$ and concentrated. Chomatography on silica gel (eluant; 1/1—ethyl acetate/hexane) affords 2.58 g (70%) of (2R)-amino-5-(1,3-dioxo-1,3-dihydroisoindol-2-yl) pentanoic acid t-butyl ester as a colorless foam: NMR ($CDCl_3$) 1.46 (s, 9H), 1.80–2.06 (m, 4H), 3.73 (t, 2H, J=6.2), 3.97 (t, 1H, J=6.3), 7.68–7.71 (m, 2H), 7.82–7.85 (m, 2H).

I. (2R)-(4'-Chlorobiphenyl-4-sulfonylamino)-5-(1,3-dioxo-1,3-dihydroisoindol-2-yl)pentanoic acid t-butyl ester

1. 4'-Chlorobiphenyl-4-sulfonyl chloride

A solution of 4-chlorophenylbenzene (7.02 g, 37.2 mmol) in 70 mL of dichloromethane is treated with chlorosulfonic acid (4.55 g, 39.1 mmol) at RT. The reaction is stirred for 2 h further, and the formed precipitate is collected by vacuum filtration, washed with dichloromethane and dried to afford 9.6 g (96%) of 4'-chlorobiphenyl-4-sulfonic acid as a white solid.

A suspension of the 4'-chlorobiphenyl-4-sulfonic acid in 100 mL of thionyl chloride is heated at reflux for 6 h, and the resulting homogeneous solution is then cooled to RT. The mixture is concentrated under reduced pressure and the residue is triturated with diethyl ether and dried to afford 9.8 g (95%) of 4'-chlorobiphenyl-4-sulfonyl chloride as an off-white solid.

2. (2R)-(4'-Chlorobiphenyl-4-sulfonylamino)-5-(1,3-dioxo-1,3-dihydroisoindol-2-yl)pentanoic acid t-butyl ester A solution of the title H compound, (2R)-amino-5-(1,3-dioxo-1,3-dihydroisoindol-2-yl)pentanoic acid t-butyl ester (1.02 g, 3.19 mmol) and triethylamine (1.34 mL, 9.61 mmol) in 20 mL of dichloromethane is treated with the title 1 compound, 4'-chlorobiphenyl-4-sulfonyl chloride (0.92 g, 3.19 mmol) at 0° C. After stirring at this temperature for 30 min, then at RT for 16 h, the solution is washed with 35 mL of 2M aqueous HCl and the organic solution is washed with brine, dried over anhydrous $Na_2SO_4$ and concentrated under reduced pressure. Chomatography on silica gel (eluant; ethyl acetate) affords 0.96 g (53%) of (2R)-(4'-chlorobiphenyl-4-sulfonylamino)-5-(1,3-dioxo-1,3-dihydroisoindol-2-yl)pentanoic acid t-butyl ester as a waxy, white solid: NMR ($CDCl_3$) 1.21 (s, 9H), 1.60–1.68 (br m, 1H), 1.75–1.84 (br m, 3H), 3.68–3.74 (m, 2H), 3.82–3.92 (m, 1H), 5.24 (d, 1H, J=9.2), 7.44 (d, 2H, J=8.6), 7.49 (d, 2H, J=8.6), 7.65 (d, 2H, J=8.5), 7.70–7.74 (m, 2H), 7.83–7.86 (m, 2H), 7.92 (d, 2H, J=8.5); IR 1774, 1712, 1348, 1162; ESI-MS 569 ($M^+$+1).

J. (2R)-(4'-Chlorobiphenyl-4-sulfonylamino)-5-(1,3-dioxo-1,3-dihydroisoindol-2-yl)pentanoic acid A solution of the title I compound, (2R)-(4'-chlorobiphenyl-4-sulfonylamino)-5-(1,3-dioxo-1,3-dihydroisoindol-2-yl)pentanoic acid t-butyl ester (0.96 g, 1.69 mmol) in TFA (10 mL, 130 mmol) is stirred at RT for 2.5 h. The solution is concentrated under reduced pressure to give a white solid which is triturated from 20 mL of diethyl ether, collected by filtration and dried to give 837 mg (97%) of (2R)-(4'-chlorobiphenyl-4-sulfonylamino)-5-(1,3-dioxo-1,3-dihydroisoindol-2-yl)pentanoic acid as a white solid: m.p. 179–181° C.; NMR(1:100 $CD_3OD/CDCl_3$) 1.65–1.86 (m, 4H), 3.63 (t, 3H, J=6.4), 3.93 (t, 3H, J=6.4), 7.39 (d, 2H, J=8.6), 7.47 (d, 2H, J=8.6), 7.60 (d, 2H, J=8.4), 7.65–7.68 (m, 2H), 7.76–7.79 (m, 2H), 7.86 (d, 2H, J=8.4); IR 1772, 1708, 1340, 1153; ESI-MS 511 ($M^-$-1), 513 ($M^+$+1).

EXAMPLE 2

(2R)-(4'-Chlorobiphenyl-4-sulfonylamino)-5-(1,3-dioxo-1,3-dihydroisoindol-2-yl)pentanoic acid hydroxyamide

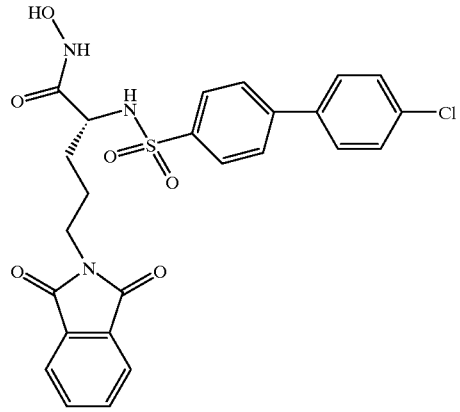

A. (2R)-(4'-Chlorobiphenyl-4-sulfonylamino)-5-(1,3-dioxo-1,3-dihydroisoindol-2-yl)pentanoic acid O-tritylhydroxyamide A solution of the title compound of Example 1, (2R)-(4'-chlorobiphenyl-4-sulfonylamino)-5-(1,3-dioxo-1,3-dihydroisoindol-2-yl)pentanoic acid (304 mg, 0.593 mmol) and NMM (0.330 mL, 3.00 mmol) in 10 mL of dichloromethane is treated with 1-hydroxy-7-azabenzotriazole (89 mg, 0.654 mmol) and 1-(3-dimethylaminopropyl)-3-ethylcarbodiimide hydrochloride (170 mg, 0.886 mmol) at RT. After stirring for 30 min, O-tritylhydroxylamine (489 mg, 1.776 mmol) is added, and the reaction is stirred for 16 h. The mixture is partitioned between 60 mL of dichloromethane and 40 mL of water. The organic solution is washed with 30 mL of 1M aqueous $NaHCO_3$, dried over anhydrous $Na_2SO_4$ and concentrated. Chomatography on silica gel (eluant; 4/6—ethyl acetate/hexane) affords 293 mg (64%) of (2R)-(4'-chlorobiphenyl-4-sulfonylamino)-5-(1,3-dioxo-1,3-dihydroisoindol-2-yl)pentanoic acid O-tritylhydroxyamide as a waxy solid: NMR($CDCl_3$) 0.62–0.76 (br m, 1H), 1.08–1.24 (br m, 1H), 1.46–1.65 (br m, 1H), 1.72–1.87 (br m, 1H), 3.65–3.73 (m, 2H), 3.94 (t, 1H, J=8.7), 5.31 (d, 1H, J=9.2), 7.20–7.27 (m, 15H), 7.48 (d, 4H, J=8.4), 7.59 (d, 2H, J=8.5), 7.70 (d, 4H, J=8.3), 7.91 (d, 2H, J=8.3), 8.27 (s, 1H); IR 1770, 1710, 1349, 1166; ESI-MS 770 ($M^+$+1).

B. (2R)-(4'-Chlorobiphenyl-4-sulfonylamino)-5-(1,3-dioxo-1,3-dihydroisoindol-2-yl)pentanoic acid hydroxyamide A solution of the title A compound, (2R)-(4'-chlorobiphenyl-4-sulfonylamino)-5-(1,3-dioxo-1,3-dihydroisoindol-2-yl)pentanoic acid O-tritylhydroxyamide (288 mg, 0.374 mmol) in 3 mL of dichloromethane is treated sequentially with triethylsilane (0.119 mL, 0.745 mmol) and trifluoroacetic acid (0.225 mL, 2.92 mmol) at 0° C. After 10 min, the solution is concentrated at 0° C. in a stream of nitrogen, and the residue is triturated from 5 mL of diethyl ether. The product is collected by vacuum filtration and dried to give 162.3 mg (82%) of (2R)-(4'-chlorobiphenyl-4-sulfonylamino)-5-(1,3-dioxo-1,3-dihydroisoindol-2-yl) pentanoic acid hydroxyamide as a white solid: m.p. 204–206° C. (dec); NMR(DMSO-$d_6$) 1.24–1.33 (br m, 1H), 1.37–1.50 (br m, 3H), 3.39–3.47 (m, 2H), 3.52–3.62 (m, 1H), 7.53 (d, 2H, J=8.3), 7.70 (d, 2H, J=8.3), 7.80 (br s, 8H), 8.12 (d, 1H, J=8.5), 8.82 (br s, 1H), 10.56 (s, 1H); IR 1772, 1341, 1159; ESI-MS 528 (M$^+$+1).

EXAMPLE 3

(2R)-(4'-Chlorobiphenyl-4-sulfonylamino)-5-(1,1,3-trioxo-2,3-dihydrobenzoisothiazol-2-yl)pentanoic acid

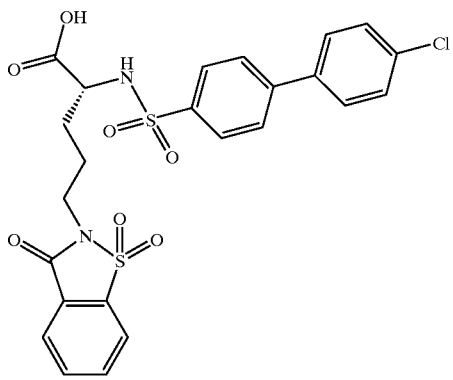

The title compound is obtained as a white solid analogously as described in Example 1: m.p. 177–179° C.; NMR(CDCl$_3$) 1.70–1.83 (m, 1H), 1.88–2.00 (m, 3H), 3.77 (q, 2H, J=6.3), 4.05–4.13 (m, 1H), 5.36 (d, 1H, J=8.6), 7.42 (d, 2H, J=8.4), 7.52 (d, 2H, J=8.4), 7.65 (d, 2H, J=8.5), 7.80–7.92 (m, 3H), 7.91 (d, 2H, J=8.2), 8.02 (d, 1H, J=7.2); IR 1776, 1733, 1338, 1188; ESI-MS 547 (M$^-$−1), 549 (M$^+$+1).

EXAMPLE 4

(2R)-(4'-Chlorobiphenyl-4-sulfonylamino)-5-(1,2,3,4-tetrahydro-1-methyl-2,4-dioxoquinazolin-3-yl) pentanoic acid

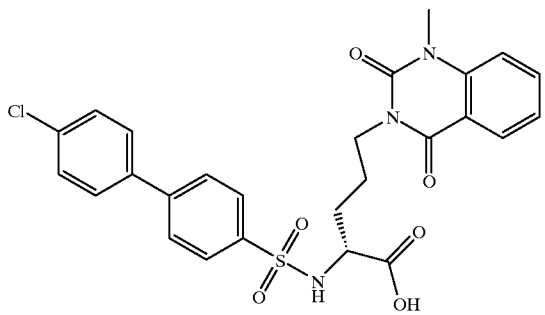

The title compound is obtained as a white solid analogously as described in Example 1: m.p. 188–191° C.; NMR(DMSO-d$_6$) 1.44–1.68 (m, 4H), 3.47 (s, 3H), 3.67–3.78 (m, 1H), 3.79–3.89 (m, 2H), 7.27 (t, 1H, J=7.5), 7.40 (d, 1H, J=8.6), 7.52 (d, 2H, J=8.6), 7.71 (d, 2H, J=8.5), 7.67–7.79 (m, 1H), 7.81 (s, 4H), 8.01 (d, 1H, J=6.8), 8.20 (d, 1H, J=8.8), 12.62 (br s, 1H); IR 1734, 1702, 1627, 1337, 1164; ESI-MS 540 (M$^-$−1), 542 (M$^+$+1).

1,2,3,4-Tetrahydro-1-methyl-2,4-dioxoquinazoline is prepared as follows:

A mixture of methyl 2-methylaminobenzoate (4.95 g, 30 mmol), sodium isocyanate (3.9 g, 60 mmol) and acetic acid (30 mL) is stirred at RT for 24 h. The precipitated product is collected by vacuum filtration, washed with water and diethyl ether and dried to give 1,2,3,4-tetrahydro-1-methyl-2,4-dioxoquinazoline (3.25 g, 62%) as a white solid.

EXAMPLE 5

(2R)-(4-Biphenylsulfonylamino)-5-(1,2,3,4-tetrahydro-1-methyl-2,4-dioxoquinazolin-3-yl) pentanoic acid

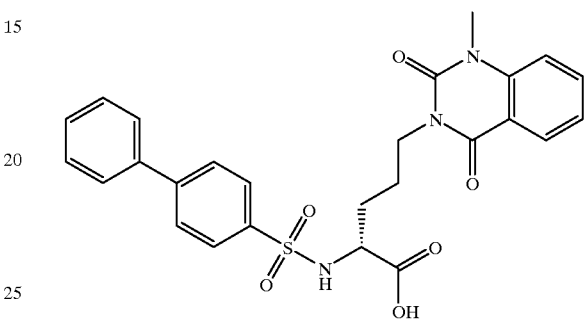

The title compound is obtained as a white solid analogously as described in Example 1: m.p. 222–224° C.; IR 1737, 1700, 1652, 1328, 1160; ESI-MS 506 (M$^-$−1).

EXAMPLE 6

(2R)-(4'-Chlorobiphenyl-4-sulfonylamino)-5-(3,4,4-trimethyl-2,5-dioxoimidazolin-1-yl)pentanoic acid

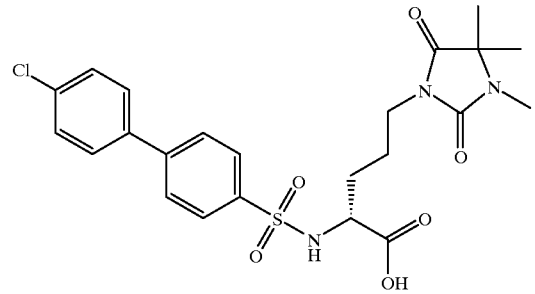

The title compound is obtained as a white solid analogously as described in Example 1: m.p. 68–71° C.; NMR (CDCl3) 1.34 (s, 6H), 1.55–1.81 (m, 4H), 2.84 (s, 3H), 3.50–3.56 (br m, 2H), 4.10 (q, 2H, J=7.2), 5.52 (d, 1H, J=8.8), 7.42 (d, 2H, J8.4), 7.52 (d, 2H, J=8.4), 7.65 (d, 2H, J=8.3), 7.89 (d, 2H, J=8.3); IR 1772, 1341, 1159; ESI-MS 528 (M$^+$+1).

3,4,4-Trimethyl-2,5-dioxoimidazolidine is prepared according to a known procedure as described in U.S. Pat. No. 1,337,269.

EXAMPLE 7

(2R)-(4'-Chlorobiphenyl-4-sulfonylamino)-5-(4-methylbenzenesulfonylamino)pentanoic acid

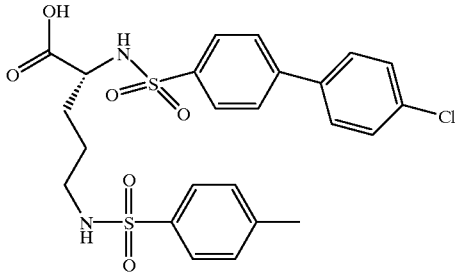

The title compound is obtained as a white solid analogously as described in Example 1: m.p. 62° C.; IR 1725, 1596, 1327, 1160; ESI-MS 535 (M⁻−1).

EXAMPLE 8

(4R)-N-[4-(4'-Chlorobiphenyl-4-sulfonylamino)-4-carboxybutyl]phthalamic acid

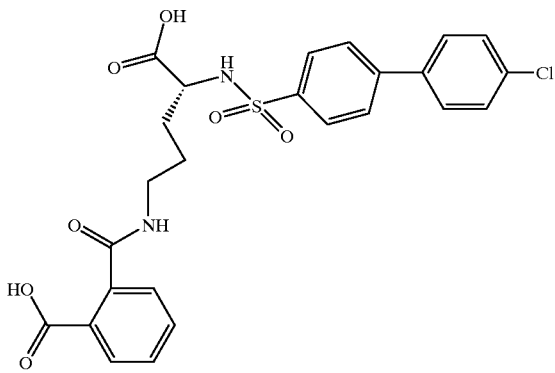

A solution of the title compound of Example 1, (2R)-(4-chlorobiphenyl-4-sulfonylamino)-5-(1,3-dioxo-1,3-dihydroisoindol-2-yl)pentanoic acid (20.0 mg, 0.039 mmol), in 2 mL of tetrahydrofuran is treated with 1M aqueous lithium hydroxide. After 2 h, the solution is acidified with 0.2 mL of 1N aqueous HCl, and the mixture is concentrated to an oil. Chomatography on LiChoprep DIOL (eluant; ethyl acetate) affords 12.8 mg (62%) of (4R)-N-[4-(4'-chlorobiphenyl-4-sulfonylamino)-4-carboxybutyl] phthalamic acid as a white solid: m.p. 119–121° C. (dec); IR 1737, 1701, 1649, 1344, 1168; ESI-MS 529 (M⁻−1).

EXAMPLE 9

5-(1,3-Dioxo-1,3-dihydroisoindol-2-yl)-(2R)-(4-phenyloxybenzenesulfonylamino)pentanoic acid

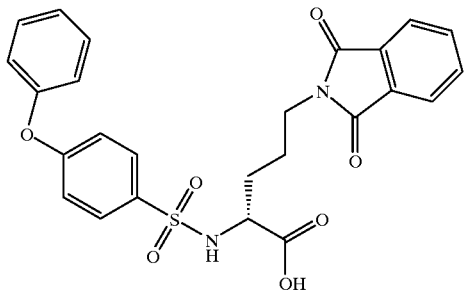

The title compound is obtained as a white solid analogously as described in Example 1: m.p. 139–140° C.; IR 1769, 1734, 1701, 1344, 1160; ESI-MS 493 (M⁻−1).

EXAMPLE 10

5-(1,3-Dioxo-1,3-dihydroisoindol-2-yl)-(2R)-(4-ethoxybenzenesulfonylamino)pentanoic acid

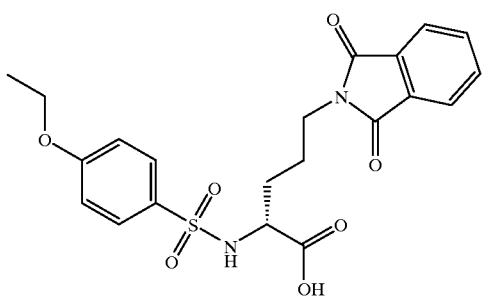

The title compound is obtained as a white solid analogously as described in Example 1: m.p. 151–152° C.; IR 1779, 1714, 1354, 1147; ESI-MS 445 (M⁻−1).

EXAMPLE 11

5-(1,3-Dioxo-1,3-dihydroisoindol-2-yl)-(2R)-[4-(pyridin-4-yloxy)benzenesulfonylamino]pentanoic acid

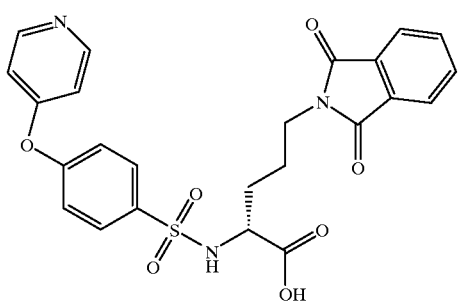

The title compound is obtained analogously as described in Example 1.

EXAMPLE 12

5-(1,3-Dioxo-1,3-dihydroisoindol-2-yl)-(2R)-[4-(4-imidazol-1-ylphenoxy)benzenesulfonylamino] pentanoic acid

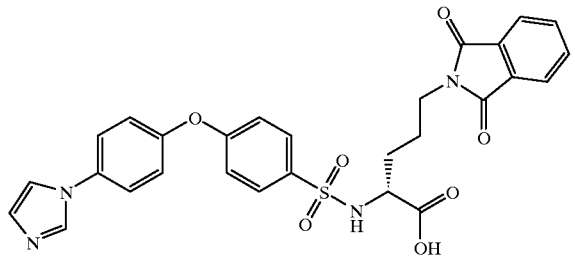

The title compound is obtained analogously as described in Example 1.

EXAMPLE 13

(2R)-[4-(4-Chlorophenyloxy)benzenesulfonylamino]-5-(1,3-dioxo-1,3-dihydroisoindol-2-yl)pentanoic acid

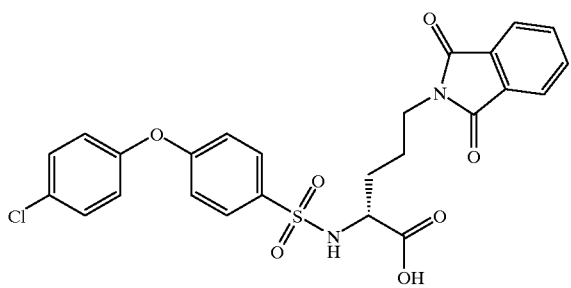

The title compound is obtained analogously as described in Example 1.

EXAMPLE 14

5-(1,3-Dioxo-1,3-dihydroisoindol-2-yl)-(2R)-[4-(4-methylpiperazin-1-yl)benzenesulfonylamino] pentanoic acid

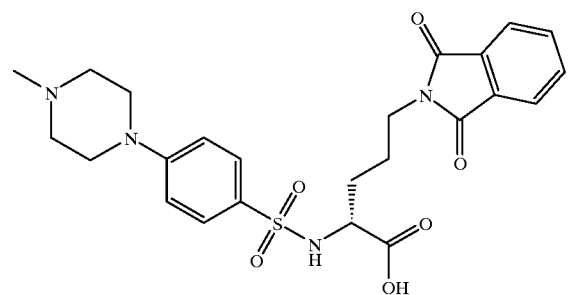

The title compound is obtained analogously as described in Example 1.

EXAMPLE 15

5-(1,3-Dioxo-1,3-dihydroisoindol-2-yl)-(2R)-[4-(4-methoxybenzoylamino)benzenesulfonylamino] pentanoic acid

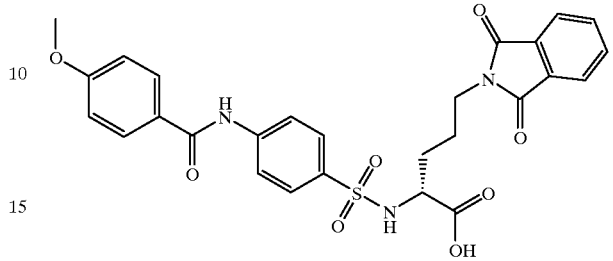

The title compound is obtained analogously as described in Example 1.

EXAMPLE 16

5-(1,3-Dioxo-1,3-dihydroisoindol-2-yl)-(2R)-[4-(4-phenylpiperidin-1-yl)benzenesulfonyamino] pentanoic acid

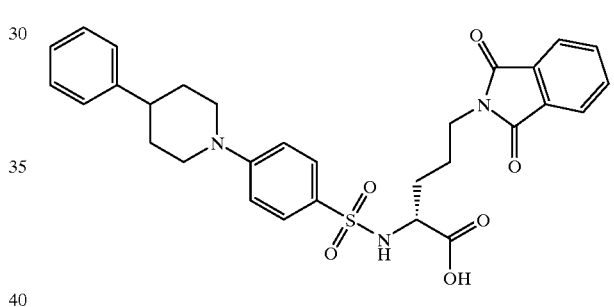

The title compound is obtained analogously as described in Example 1.

EXAMPLE 17

5-(1,3-Dioxo-1,3-dihydroisoindol-2-yl)-(2R)-[4-(benzenesulfonyl)thiophene-2-sulfonylamino] pentanoic acid

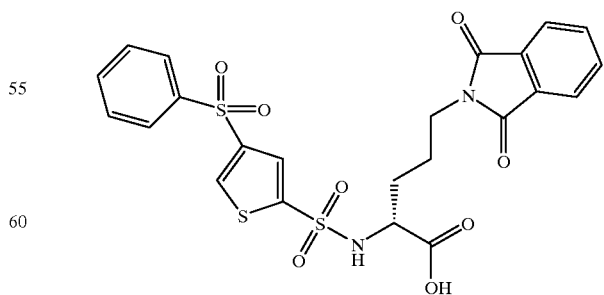

The title compound is obtained analogously as described in Example 1.

EXAMPLE 18

5-(1,3-Dioxo-1,3-dihydroisoindol-2-yl)-(2R)-[5-(benzenesulfonyl)thiophene-2-sulfonylamino]pentanoic acid

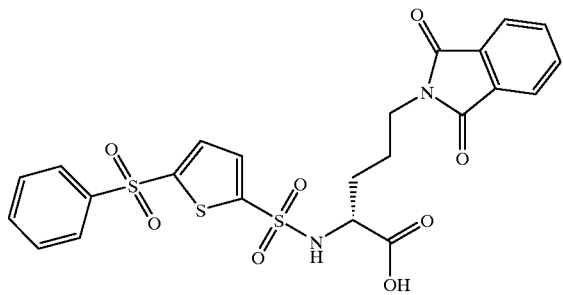

The title compound is obtained analogously as described in Example 1.

EXAMPLE 19

5-(1,3-Dioxo-1,3-dihydroisoindol-2-yl)-(2R)-[5-(5-triluoromethylpyridine-2-sulfonyl)thiophene-2-sulfonylamino]pentanoic acid

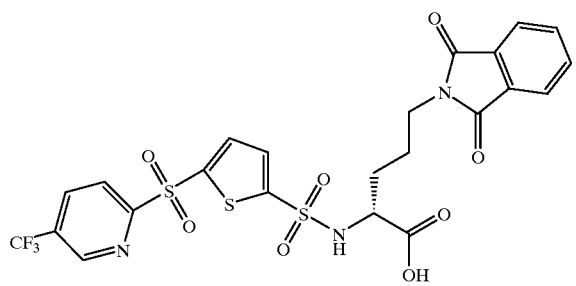

The title compound is obtained analogously as described in Example 1.

EXAMPLE 20

(2R)-[4-(Pyridin-4-yloxy)benzenesulfonylamino]-5-(1,1,3-trioxo-2,3-dihydrobenzoisothiazol-2-yl)pentanoic acid

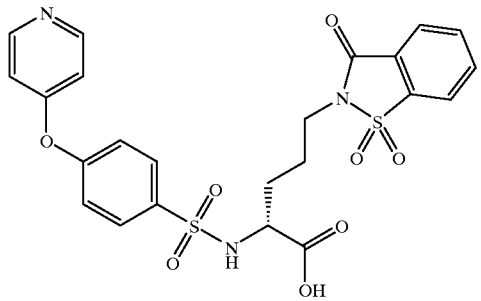

The title compound is obtained analogously as described in Example 1.

EXAMPLE 21

(2R)-[4-(4-Imidazol-1-ylphenoxy)benzenesulfonylamino]-5-(1,1,3-trioxo-2,3-dihydrobenzoisothiazol-2-yl)pentanoic acid

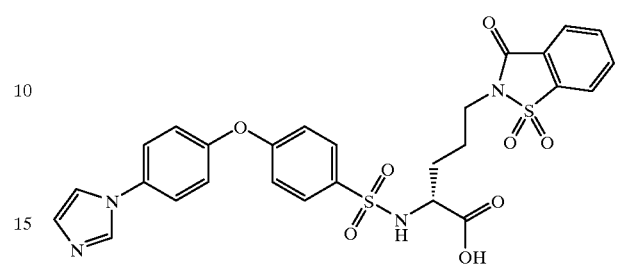

The title compound is obtained analogously as described in Example 1.

EXAMPLE 22

(2R)-[4-(4-Chlorophenyloxy)benzenesulfonylamino]-5-(1,1,3-trioxo-2,3-dihydrobenzoisothiazol-2-yl)pentanoic acid

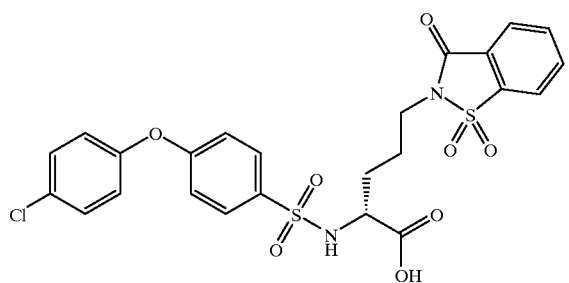

The title compound is obtained analogously as described in Example 1.

EXAMPLE 23

(2R)-(4-Methylpiperazin-1-ylbenzenesulfonylamino)-5-(1,1,3-trioxo-2,3-dihydrobenzoisothiazol-2-yl)pentanoic acid

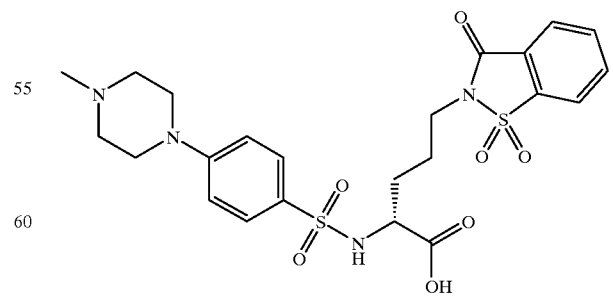

The title compound is obtained analogously as described in Example 1.

EXAMPLE 24

(2R)-[4-(4-Methoxybenzoylamino)
benzenesulfonylamino]-5-(1,1,3-trioxo-2,3-
dihydrobenzoisothiazol-2-yl)pentanoic acid

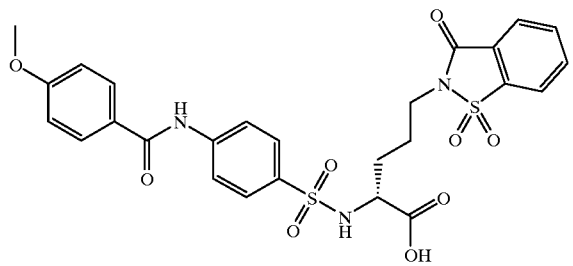

The title compound is obtained analogously as described in Example 1.

EXAMPLE 25

(2R)-[4-(4-Phenylpiperidin-1-yl)
benzenesulfonylamino]-5-(1,1,3-trioxo-2,3-
dihydrobenzoisothiazol-2-yl)pentanoic acid

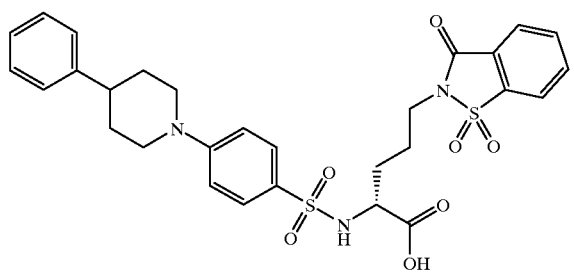

The title compound is obtained analogously as described in Example 1.

EXAMPLE 26

(2R)-(4-Benzenesulfonylthiophene-2-
sulfonylamino]-5-(1,1,3-trioxo-2,3-
dihydrobenzoisothiazol-2-yl)pentanoic acid

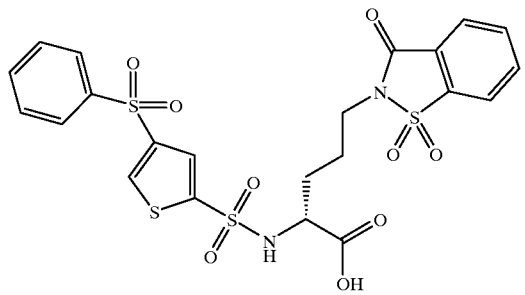

The title compound is obtained analogously as described in Example 1.

EXAMPLE 27

(2R)-(5-Benzenesulfonylthiophene-2-
sulfonylamino]-5-(1,1,3-trioxo-2,3-
dihydrobenzoisothiazol-2-yl)pentanoic acid

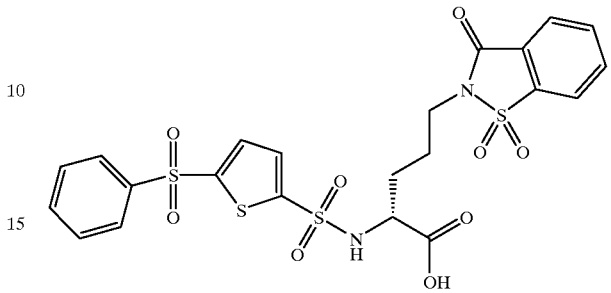

The title compound is obtained analogously as described in Example 1.

EXAMPLE 28

(2R)-[5-(5-Trifluoromethylpyridine-2-sulfonyl)
thiophene-2-sulfonylamino]-5-(1,1,3-trioxo-2,3-
dihydrobenzoisothiazol-2-yl)pentanoic acid

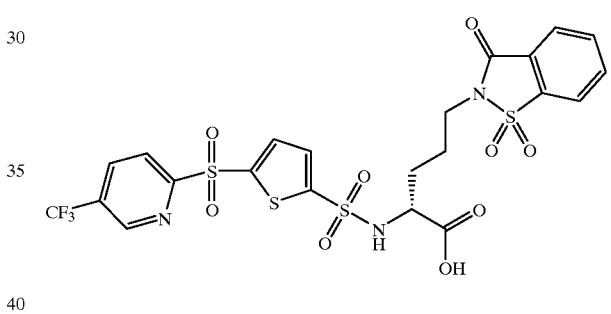

The title compound is obtained analogously as described in Example 1.

EXAMPLE 29

(2R)-(4'-Chlorobiphenyl-4-sulfonylamino)-3-{[(1,1,
3-trioxo-2,3-dihydrobenzoisothiazol-2-yl)methyl]
thio}propionic acid

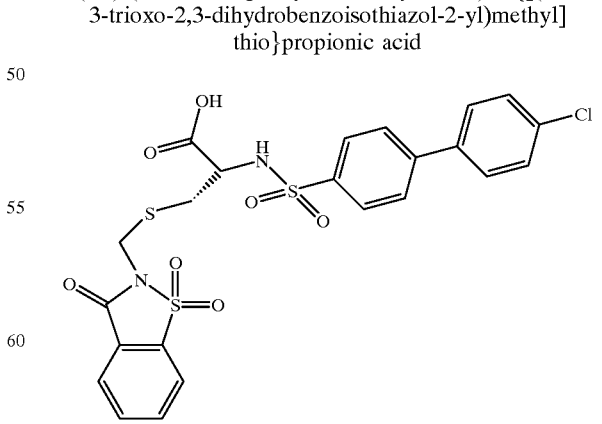

The title compound is obtained analogously as described in Example 1.

EXAMPLE 30

(2R)-(4'-Chlorobiphenyl-4-sulfonylamino)-5-(1,1,3-trioxo-2,3-dihydrobenzoisothiazol-2-yl)pentanoic acid hydroxyamide

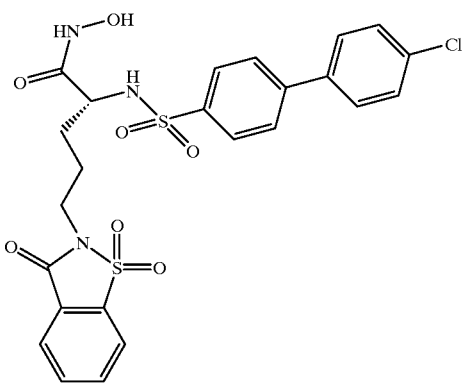

The title compound is obtained as a white solid analogously as described in Example 2: m.p. 200–205° C. (dec); IR 1730, 1668, 1336, 1162; ESI-MS 564 (M$^+$+1).

EXAMPLE 31

(2R)-(4'-Chlorobiphenyl-4-sulfonylamino)-5-(1,2,3,4-tetrahydro-1-methyl-2,4-dioxoquinazolin-3-yl) pentanoic acid hydroxyamide

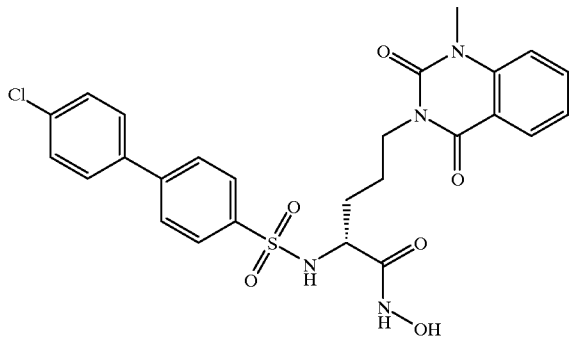

The title compound is obtained as a white solid analogously as described in Example 2: m.p. 235° C.; IR 1702, 1658, 1336, 1160; ESI-MS 557 (M$^+$+1).

EXAMPLE 32

(2R)-(4-Biphenylsulfonylamino)-5-(1,2,3,4-tetrahydro-1-methyl-2,4-dioxoquinazolin-3-yl) pentanoic acid hydroxyamide

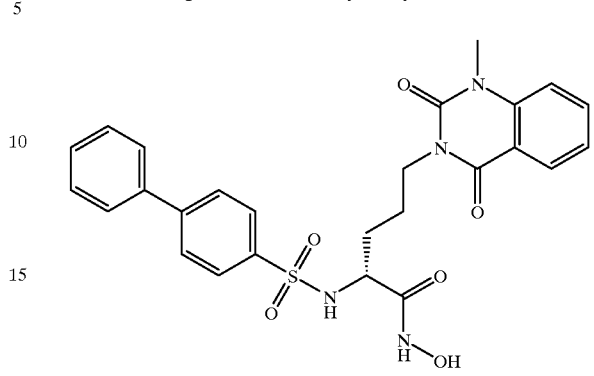

The title compound is obtained as a white solid analogously as described in Example 2: m.p. 202–203° C.; IR 1704, 1660, 1336, 1160; ESI-MS 523 (M$^+$+1).

EXAMPLE 33

5-(1,3-Dioxo-1,3-dihydroisoindol-2-yl)-(2R)-[4-(pyridin-4-yloxy)benzenesulfonylamino]pentanoic acid hydroxyamide

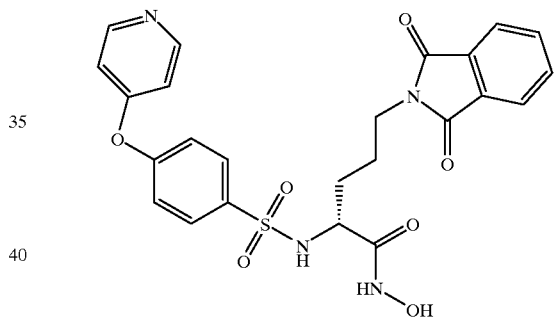

The title compound is obtained analogously as described in Example 2.

EXAMPLE 34

5-(1,3-Dioxo-1,3-dihydroisoindol-2-yl)-(2R)-[4-(4-imidazol-1-ylphenoxy)benzenesulfonylamino] pentanoic acid hydroxyamide

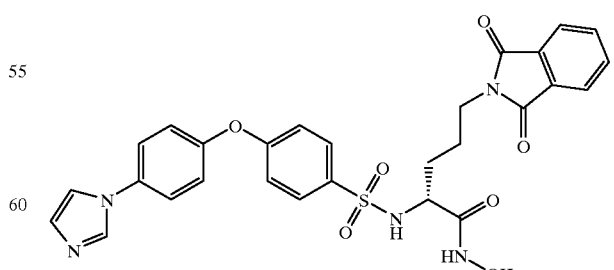

The title compound is obtained analogously as described in Example 2.

EXAMPLE 35

(2R)-[4-(4-Chlorophenyloxy)benzenesulfonylamino]-5-(1,3-dioxo-1,3-dihydroisoindol-2-yl)pentanoic acid hydroxyamide

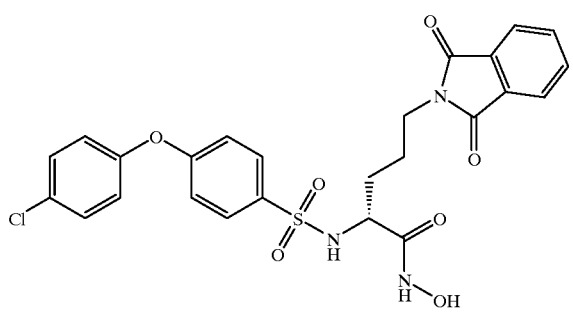

The title compound is obtained analogously as described in Example 2.

EXAMPLE 36

5-(1,3-Dioxo-1,3-dihydroisoindol-2-yl)-(2R)-[4-(4-methylpiperazin-1-yl)benzenesulfonylamino]pentanoic acid hydroxyamide

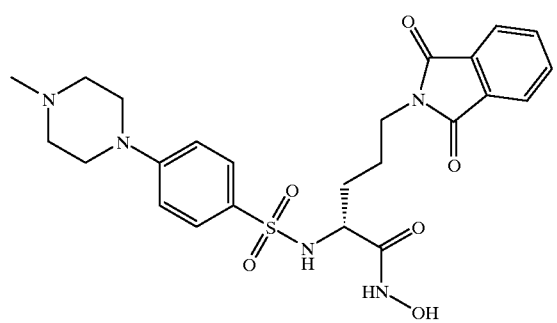

The title compound is obtained analogously as described in Example 2.

EXAMPLE 37

5-(1,3-Dioxo-1,3-dihydroisoindol-2-yl)-(2R)-[4-(4-methoxybenzoylamino)benzenesulfonylamino]pentanoic acid hydroxyamide

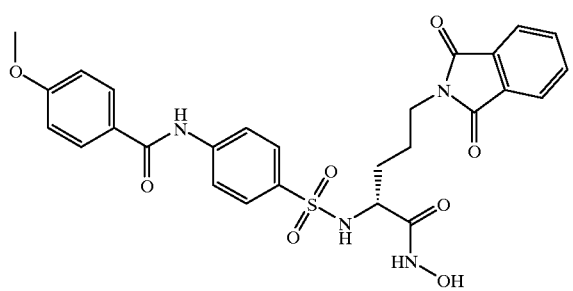

The title compound is obtained analogously as described in Example 2.

EXAMPLE 38

5-(1,3-Dioxo-1,3-dihydroisoindol-2-yl)-(2R)-[4-(4-phenylpiperidin-1-yl)benzenesulfonyamino]pentanoic acid hydroxyamide

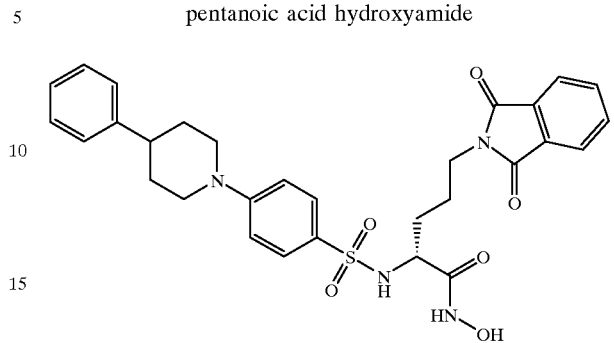

The title compound is obtained analogously as described in Example 2.

EXAMPLE 39

5-(1,3-Dioxo-1,3-dihydroisoindol-2-yl)-(2R)-(4-benzenesulfonylthiophene-2-sulfonylamino]pentanoic acid hydroxyamide

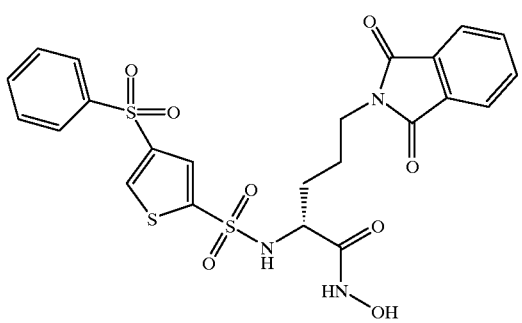

The title compound is obtained analogously as described in Example 2.

EXAMPLE 40

5-(1,3-Dioxo-1,3-dihydroisoindol-2-yl)-(2R)-(5-benzenesulfonylthiophene-2-sulfonylamino]pentanoic acid hydroxyamide

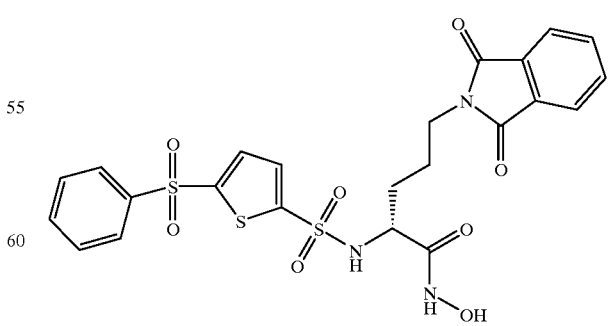

The title compound is obtained analogously as described in Example 2.

EXAMPLE 41

5-(1,3-Dioxo-1,3-dihydroisoindol-2-yl)-(2R)-[5-(5-trifluoromethylpyridine-2-sulfonyl)thiophene-2-sulfonylamino]pentanoic acid hydroxyamide

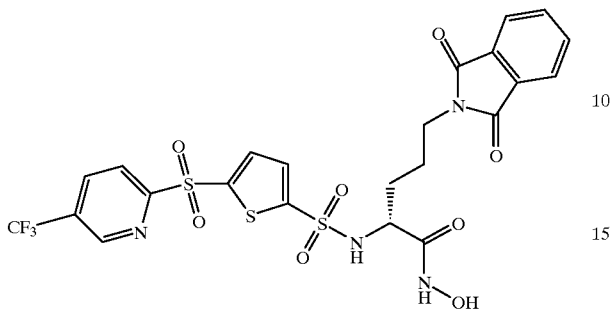

The title compound is obtained analogously as described in Example 2.

EXAMPLE 42

(2R)-[4-(Pyridin-4-yloxy)benzenesulfonylamino]-5-(1,1,3-trioxo-2,3-dihydrobenzoisothiazol-2-yl)pentanoic acid hydroxyamide

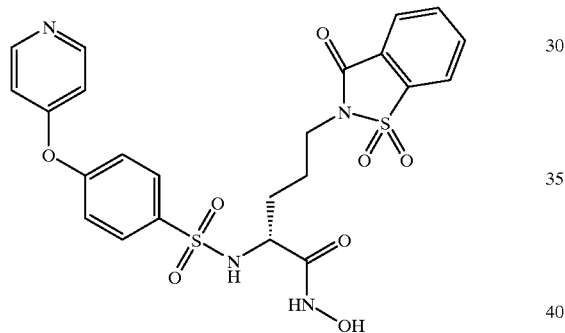

The title compound is obtained analogously as described in Example 2.

EXAMPLE 43

(2R)-[4-(4-Imidazol-1-ylphenoxy)benzenesulfonylamino]-5-(1,1,3-trioxo-2,3-dihydrobenzoisothiazol-2-yl)pentanoic acid hydroxyamide

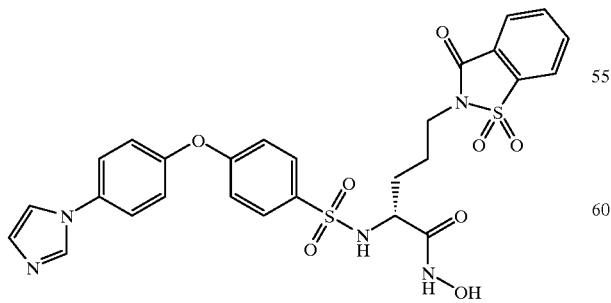

The title compound is obtained analogously as described in Example 2.

EXAMPLE 44

(2R)-[4-(4-Chlorophenyloxy)benzenesulfonylamino]-5-(1,1,3-trioxo-2,3-dihydrobenzoisothiazol-2-yl)pentanoic acid hydroxyamide

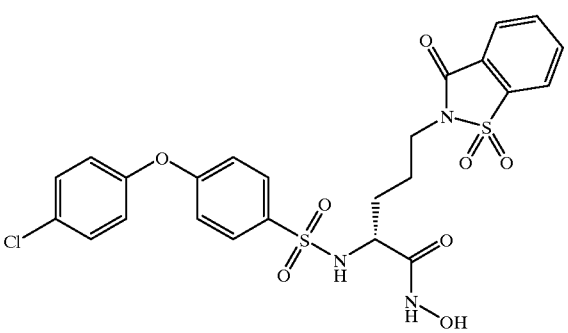

The title compound is obtained analogously as described in Example 2.

EXAMPLE 45

(2R)-[(4-Methylpiperazin-1-ylbenzenesulfonylamino]-5-(1,1,3-trioxo-2,3-dihydrobenzoisothiazol-2-yl)pentanoic acid hydroxyamide

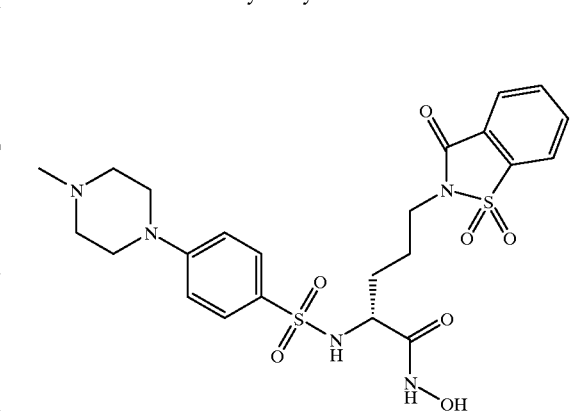

The title compound is obtained analogously as described in Example 2.

EXAMPLE 46

(2R)-[4-(4-Methoxybenzoylamino)benzenesulfonylamino]-5-(1,1,3-trioxo-2,3-dihydrobenzoisothiazol-2-yl)pentanoic acid hydroxyamide

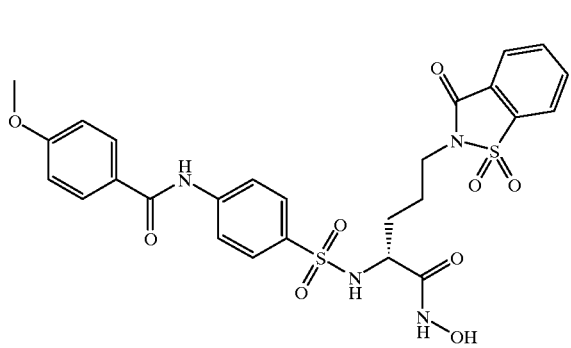

The title compound is obtained analogously as described in Example 2.

EXAMPLE 47

(2R)-[4-(4-Phenylpiperidin-1-yl)benzenesulfonylamino]-5-(1,1,3-trioxo-2,3-dihydrobenzoisothiazol-2-yl)pentanoic acid hydroxyamide

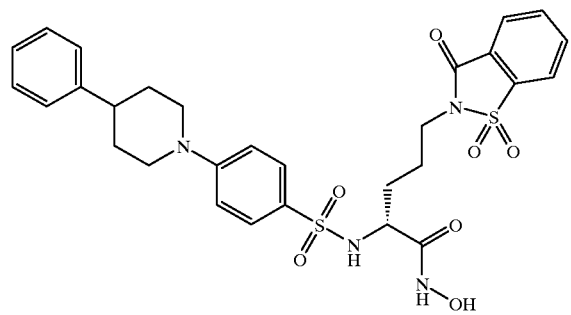

The title compound is obtained analogously as described in Example 2.

EXAMPLE 48

(2R)-(4-Benzenesulfonylthiophene-2-sulfonylamino]-5-(1,1,3-trioxo-2,3-dihydrobenzoisothiazol-2-yl)pentanoic acid hydroxyamide

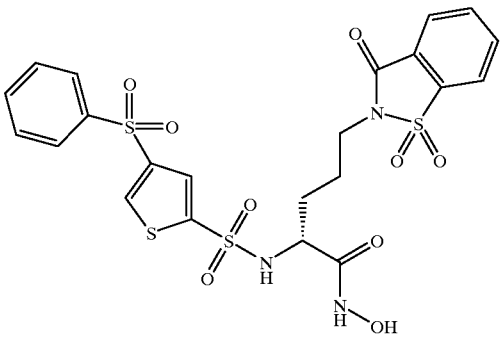

The title compound is obtained analogously as described in Example 2.

EXAMPLE 49

(2R)-(5-Benzenesulfonylthiophene-2-sulfonylamino]-5-(1,1,3-trioxo-2,3-dihydrobenzoisothiazol-2-yl)pentanoic acid hydroxyamide

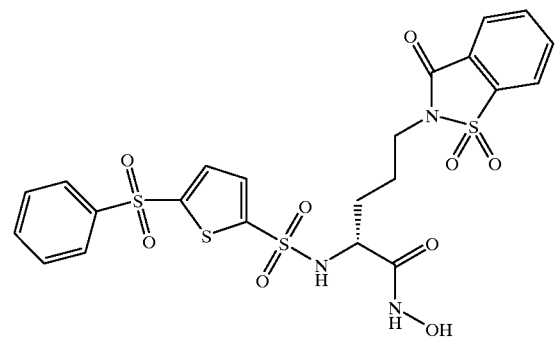

The title compound is obtained analogously as described in Example 2.

EXAMPLE 50

(2R)-[5-(5-Trifluoromethylpyridine-2-sulfonyl)thiophene-2-sulfonylamino]-5-(1,1,3-trioxo-2,3-dihydrobenzoisothiazol-2-yl)pentanoic acid hydroxyamide

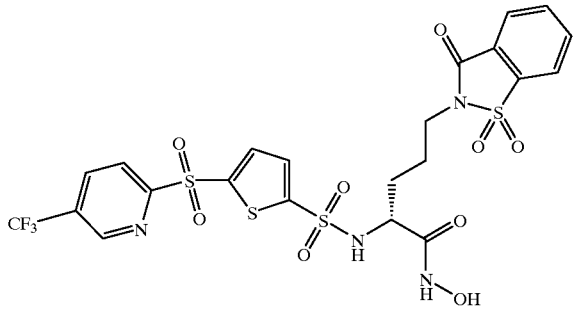

The title compound is obtained analogously as described in Example 2.

EXAMPLE 51

(2R)-(4'-Chlorobiphenyl-4-sulfonylamino)-3-{[(1,1,3-trioxo-2,3-dihydrobenzoisothiazol-2-yl)methyl]thio}propionic acid hydroxyamide

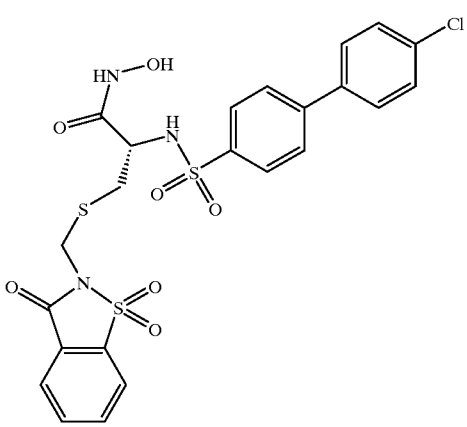

The title compound is obtained analogously as described in Example 2.

EXAMPLE 52

(2R,S)-(4'-Chlorobiphenyl-4-sulfonylamino)-6-(1,2,3,4-tetrahydro-1-methyl-2,4-dioxoquinazolin-3-yl)hexanoic acid

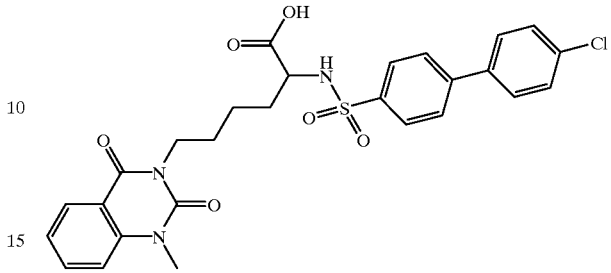

A. 3-(4-Bromobutyl)-1,2,3,4-tetrahydro-1-methyl-2,4-dioxoquinazoline and 3-(4-chlorobutyl)-1,2,3,4-tetrahydro-1-methyl-2,4-dioxoquinazoline A stirred solution of 1,2,3,4-tetrahydro-1-methyl-2,4-dioxoquinazoline (1.60 g, 9.08 mmol) in 25 mL of DMF is treated in one portion with sodium hydride (60% in mineral oil, 0.40 g, 10.0 mmol). After stirring the mixture at RT for 1 h and at 50° C. for 30 min, 1-bromo-4-chlorobutane (4.19 mL, 36.4 mmol) is added in one portion at 50° C., and the resulting solution is stirred at 80° C. for 16 h. The reaction mixture is poured into 100 mL of water to precipitate a white solid which is extracted with three 50 mL portions of ethyl acetate. The combined organic phases are washed with three 25 mL portions of brine, dried over anhydrous $MgSO_4$ and concentrated to give 2.35 g (81%) of a 1:1 mixture of 3-(4-bromobutyl)-1,2,3,4-tetrahydro-1-methyl-2,4-dioxoquinazoline and 3-(4-chlorobutyl)-1,2,3,4-tetrahydro-1-methyl-2,4-dioxoquinazoline as a waxy, white solid: m.p. 128° C.; NMR ($CDCl_3$) 1.80–1.97 (m, 4H), 3.44 (t, 1 H, J=6.4), 3.56–3.59 (m, 1 H), 3.60 (s, 3H), 4.12 (t, 2H, J=6.9), 7.18–7.28 (m, 2H), 7.67 (td, 1H, J=1.5, 7.9), 8.21 (dd, 1H, J=1.5, 7.9); IR 1699, 1662; ESI-MS 267 ($M^+$+1), 269 ($M^+$+3), 311 ($M^+$+1), 313 ($M^+$+3).

B. 3-(4-Iodobutyl)-1,2,3,4-tetrahydro-1-methyl-2,4-dioxoquinazoline

A solution of the title A compounds, 3-(4-bromobutyl)-1,2,3,4-tetrahydro-1-methyl-2,4-dioxoquinazoline and 3-(4-chlorobutyl)-1,2,3,4-tetrahydro-1-methyl-2,4-dioxoquinazoline (1:1 mixture; 2.35 g, 8.13 mmol) in 30 mL of methyl ethyl ketone is treated with sodium iodide (2.64 g, 17.62 mmol) at RT. The reaction is heated at reflux for 16 h, then cooled and the solvent is evaporated under reduced pressure. The residue is partitioned between 200 mL of ethyl acetate and 5 mL of water. The organic solution is washed with 10 mL of 1% aqueous sodium sulfite and 10 mL of brine, dried over anhydrous $MgSO_4$, and concentrated to give 3.10 g (100%) of 3-(4-iodobutyl)-1,2,3,4-tetrahydro-1-methyl-2,4-dioxoquinazoline as a white solid: m.p. 105–107° C.; NMR (CDCl3) 1.75–1.95 (m, 4H), 3.22 (t, 2H, J=6.8), 3.59 (s, 3H), 4.11 (t, 2H, J=7.1), 7.17–7.28 (m, 2H), 7.67 (dt, 1H, J=1.6, 7.9), 8.21 (dd, 1H, J=1.5, 7.9); IR 1702, 1658; ESI-MS 359 ($M^+$+1).

C. 2-(Benzhydrylideneamino)-6-(1,2,3,4-tetrahydro-1-methyl-2,4-dioxoquinazolin-3-yl)hexanoic acid t-butyl ester A solution of N-(diphenylmethylene)glycine t-butyl ester (1.30 g, 4.40 mmol) in 10 mL of DMF is treated with sodium hydride (60% in mineral oil, 0.250 g, 6.25 mmol) at 25° to give a red orange solution. After 1 h, the temperature is raised to 60° C. and a solution of the title B compound, 3-(4-iodobutyl)-1,2,3,4-tetrahydro-1-methyl-2,4-dioxoquinazoline (1.58 g, 4.41 mmol) in 10 mL of DMF is added dropwise over 10 min. After stirring for 5 h at 60° C. and 58 h at 25° C. the solvent is evaporated under reduced pressure, and the residue is partioned between 75 mL of ethyl acetate and 25 mL of water. The organic solution is washed with three 25 mL portions of brine, dried over anhydrous MgSO$_4$, and concentrated to give 2.15 g of 2-(benzhydrylideneamino)-6-(1,2,3,4-tetrahydro-1-methyl-2,4-dioxoquinazolin-3-yl)hexanoic acid t-butyl ester as a yellow oil.

D. 2-Amino-6-(1-methyl-2,4-dioxo-1,4-di-hydro-2H-quinazolin-3-yl)hexanoic acid t-butyl ester A solution of the title C compound, 2-(benzhydrylideneamino)-6-(1,2,3,4-tetrahydro-1-methyl-2,4-dioxoquinazolin-3-yl)hexanoic acid t-butyl ester (2.15 g) in 80 mL of acetonitrile is treated with 8 mL of water and p-toluenesulfonic acid hydrate (0.800 g, 4.21 mmol), and the clear solution is stirred at 25° C. for 16 h. The solvent is evaporated under reduced pressure, and the residue is partioned between 150 mL of diethyl ether and 100 mL of 0.1N aqueous HCl. The aqueous phase is added dropwise to 1N aqueous NaOH (15 mL, 15.0 mmol) to precipitate an oily solid which is extracted into two 60 mL portions of methylene chloride. The organic extracts are combined, dried over anhydrous MgSO$_4$, and concentrated. Chomatography on silica gel (eluant; ethyl acetate) affords 448 mg (30%) of 2-amino-6-(1-methyl-2,4-dioxo-1,4-di-hydro-2H-quinazolin-3-yl)hexanoic acid t-butyl ester as a colorless oil: NMR(CDCl$_3$) 1.46 (s, 9H), 1.51–1.79 (m, 6H), 3.32 (dd, 1H, J=7.0, 5.4), 3.61 (s, 3H), 4.11 (t, 2H, J=7.4), 7.20 (d, 1H, J=8.3), 7.25–7.29 (m, 1H), 7.69 (td, 1H, J=8.6, 1.5), 8.23 (dd, 1H, J=7.9, 1.5); IR 1702, 1656; MS 362 (M$^+$+1).

E. (2R,S)-(4'-Chlorobiphenyl-4-sulfonylamino)-6-(1,2,3,4-tetrahydro-1-methyl-2,4-dioxoquinazolin-3-yl)hexanoic acid t-butyl ester A solution of the title D compound, 2-amino-6-(1,2,3,4-tetrahydro-1-methyl-2,4-dioxoquinazolin-3-yl)hexanoic acid t-butyl ester (129 mg, 0.357 mmol) in 2 mL of THF is treated at 0° C. with triethylamine (50.8 mg, 0.502 mmol) and 4'-chlorobiphenyl-4-sulfonyl chloride (110 mg, 0.383 mmol). The clear solution is allowed to warm to RT over 2 h and is partioned between 25 mL of dichloromethane and 10 mL of brine. The organic phase is dried over anhydrous MgSO$_4$ and is concentrated under reduced pressure. Chomatography on silica gel (eluant; gradient from 30% to 50% ethyl acetate in hexanes) affords 190 mg (87%) of (2R,S)-( 4'-chlorobiphenyl-4-sulfonylamino)-6-(1,2,3,4-tetrahydro-1-methyl-2,4-dioxoquinazolin-3-yl)hexanoic acid t-butyl ester as a colorless oil: NMR(CDCl$_3$) 1.24 (s, 9H), 1.47 (q, 2H, J=7.6), 1.66–1.79 (m, 4H), 3.61 (s, 3H), 3.79–3.90 (m, 1H), 4.07 (t, 2H, J=7.4), 5.28 (d, 1H, J=9.2), 7.21 (d, 1H, J=8.2), 7.25–7.29 (m, 1H), 7.44 (d, 2H, J=8.4), 7.50 (d, 2H, J=8.4), 7.65 (d, 2H, J=8.4), 7.69 (t, 1H, J=7.2), 7.91 (d, 2H, J=8.4), 8.23 (dd, 1H, J=7.8, 1.3); IR 1727, 1702, 1658, 1349, 1166; MS 612 (M$^+$+1).

F. (2R,S)-(4'-Chlorobiphenyl-4-sulfonylamino)-6-(1,2,3,4-tetrahydro-1-methyl-2,4-dioxoquinazolin-3-yl)hexanoic acid The title compound is obtained as a white solid analogously as described in Example 1: m.p. 208–210° C.; NMR(1:100 CD$_3$OD/CDCl$_3$) 1.36–1.47 (m, 2H), 1.58–1.69 (m, 2H), 1.69–1.86 (m, 2H), 3.57 (s, 3H), 3.90 (dd, 1H, J=6.8, 5.1), 4.00 (td, 2H, J=7.0, 2.0). 7.20 (d, 1H, J=8.3), 7.23–7.28 (m, 1H), 7.40 (d, 2H, J=8.5), 7.50 (d, 2H, J=8.5), 7.68 (td, 1H, J=7.0, 0.7), 7.89 (d, 2H, J=8.3), 8.17 (dd, 1H, J=7.7, 1.1); IR 1727, 1700, 1635, 1334, 1157; ESI-MS 554 (M$^-$–1).

EXAMPLE 53

(2R,S)-(4'-Chlorobiphenyl-4-sulfonylamino)-6-(3,4,4-trimethyl-2,5-dioxoimidazolin-1-yl)hexanoic acid

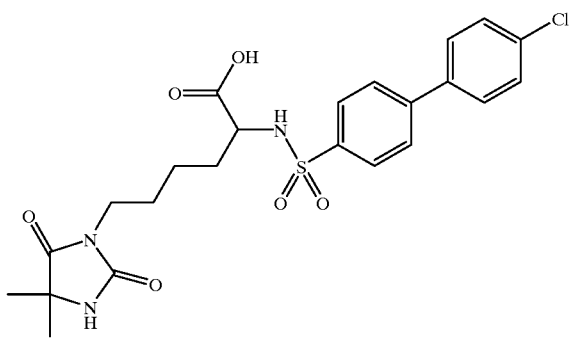

The title compound is obtained as a white solid analogously as described in Example 52: m.p. 78–80° C.; IR 1714, 1598, 1166; ESI-MS 509 (M$^+$+1).

EXAMPLE 54

(2R,S)-(4'-Chlorobiphenyl-4-sulfonylamino)-6-(1,2,3,4-tetrahydro-1-methyl-2,4-dioxoquinazolin-3-yl) hexanoic acid hydroxyamide

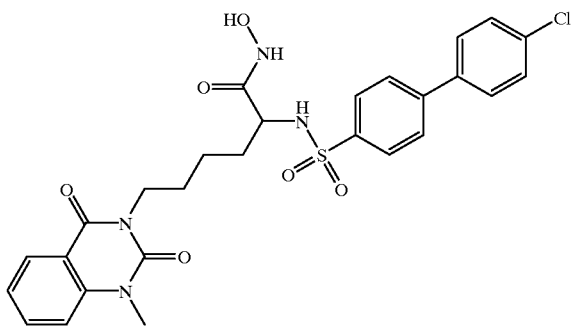

The title compound is obtained as a white solid analogously as described in Examples 2 and 52.

EXAMPLE 55

(2R,S)-(4'-Chlorobiphenyl-4-sulfonylamino)-6-(3,4, 4-trimethyl-2,5-dioxoimidazolin-1-yl)hexanoic acid hydoxyamide

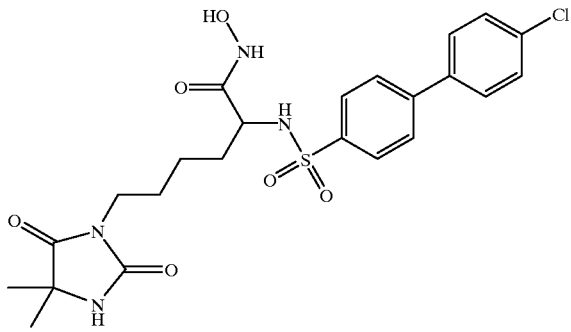

The title compound is obtained as a white solid analogously as described in Examples 2 and 52.

EXAMPLE 56

(2R)-(4'-Chlorobiphenyl-4-sulfonylamino)-4-(3,4,4-trimethyl-2,5-dioxoimidazolin-1-yl)butyric acid

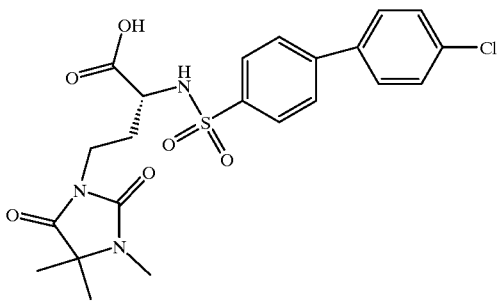

A. D-Aspartic acid β-methyl ester hydrochloride

A suspension of D-aspartic acid (10.0 g, 75.1 mmol) in 50 mL methanol is treated with thionyl chloride (8.94 g, 75.1 mmol) at 0° C. The reaction mixture is stirred at 0° C. for 30 min, then at RT for 2 h. The resulting clear solution is diluted with 200 mL diethyl ether with rapid stirring. A white precipitate is formed which is collected by vacuum filtration, washed with diethyl ether and dried to yield 10.7 g (78%) of D-aspartic acid β-methyl ester hydrochloride.

B. D-N-(4'-Chlorobiphenyl-4-sulfonyl)aspartic acid β-methyl ester

A solution of the title A compound, D-aspartic acid β-methyl ester hydrochloride (10.7 g, 58.33 mmol) in 1/1—dioxane/water (400 mL) containing triethylamine (23.61 g, 233.3 mmol) is treated with 4'-chlorobiphenyl-4-sulfonyl chloride (17.0 g, 58.33 mmol) at RT. After 16 h, the mixture is concentrated to half the original volume, then acidified to pH=1–2 by addition of 1N aqueous HCl. The product is taken up in EtOAc (2×200 mL), and the combined organic extracts are washed with brine, dried over anhydrous Na$_2$SO$_4$ and concentrated to give 20.24 g (87%) of D-N-(4'-chlorobiphenyl-4-sulfonyl)aspartic acid β-methyl ester.

C. D-N-(4'-Chlorobiphenyl-4-sulfonyl)aspartic acid α-t-butyl, β-methyl ester

N,N-Dimethylformide di-t-butyl acetal is added dropwise to a suspension of the title B compound, D-N-(4'-chlorobiphenyl-4-sulfonyl)aspartic acid β-methyl ester in 60 mL of toluene over a period of 40 min at 75° C. The resulting clear solution is heated at 80° C. for 2 h further. The reaction is allowed to cool to RT, then quenched with water, and the organic solution is washed with saturated aqueous NaHCO$_3$ and brine, dried over anhydrous Na$_2$SO$_4$ and concentrated. Chomatography on silica gel (eluant; 2/5—EtOAc/hexane) provides 11.41 g (49%) of D-N-(4'-chlorobiphenyl-4-sulfonyl)aspartic acid α-t-butyl, β-methyl ester as yellow solid.

D. D-N-t-Butyloxycarbonyl-N-(4'-chlorobiphenyl-4-sulfonyl)aspartic acid α-t-butyl, β-methyl ester A solution of di-t-butyl dicarbonate in tetrahydrofuran (30 mL) is added dropwise via an additional funnel to a mixture of the title C compound, D-N-(4'-chlorobiphenyl-4-sulfonyl)aspartic acid α-t-butyl, β-methyl ester (11.41 g, 25.14 mmol), triethylamine (7.63 g, 75.4 mmol) and 4-dimethylaminopyridine (3.07 g, 25.14 mmol) at 0° C. over a period of 30 min. The reaction mixture is stirred at 0° C. for 1 h further, then at room temperature for 3 h. The solvent is evaporated, and the residue is partitioned between EtOAc (150 mL) and 0.5N aqueous HCl (150 mL). The organic solution is washed with saturated aqueous NaHCO$_3$ and brine, dried over anhydrous Na$_2$SO$_4$ and concentrated to give D-N-t-butyloxycarbonyl-N-(4'-chlorobiphenyl-4-sulfonyl)aspartic acid α-t-butyl, β-methyl ester as yellow foam 11.47 g (83%).

E. (2R)-[t-Butoxycarbonyl(4'-chlorobiphenyl-4-sulfonyl)amino]4-hydroxybutyric acid t-butyl ester A solution of 2.0 M solution of lithium borohydride in THF (9 mL, 18.07 mmol) is added to a solution of the title D compound, D-N-t-butyloxycarbonyl-N-(4'-chlorobiphenyl-4-sulfonyl)aspartic acid α-t-butyl, β-methyl ester (4.0 g, 7.23 mmol) in 40 mL of THF at 0° C. The resulting yellow solution is stirred at 0° C. for 2 h, then treated with methanol (0.63 g, 18.07 mmol). The reaction mixture is stirred at 0° C. for 1 h further, then gradually warmed to RT. After 24 h, the reaction is recooled to 0° C. and quenched with saturated aqueous sodium carbonate (Na$_2$CO$_3$). The mixture is partitioned between EtOAc and brine, dried over anhydrous Na$_2$SO$_4$ and concentrated. The product is purified by chomatography on silica gel (eluant; 1/4—EtOAc/hexane) to provide 2.0 g (53%) of product.

F. (2R)-[t-Butyloxycarbonyl(4'-chlorobiphenyl-4-sulfonyl)amino]-4-iodobutyric acid t-butyl ester A solution of the title E compound, (2R)-[t-butoxycarbonyl(4'-chlorobiphenyl-4-sulfonyl)amino]4-hydroxybutyric acid t-butyl ester (2.0 g, 9.58 mmol) in 50 mL dichloromethane is sequentially treated with iodine (2.88 g, 14.37 mmol), triphenylphosphine (3.72 g, 14.37 mmol) and imidazole (0.97 g, 14.37 mmol) at RT. After 2 h, 20 mL of methanol are added and the reaction mixture is stirred at RT for 30 min further. The solvent is evaporated and the product is purified by chomatography on silica gel (eluant; 1/19—EtOAc/hexane) to afford 2.46 g (78%) of (2R)-[t-butyloxycarbonyl(4'-chlorobiphenyl-4-sulfonyl)amino]-4-iodobutyric acid t-butyl ester.

G. (2R)-[t-Butyloxycarbonyl(4'-chlorobiphenyl-4-sulfonylamino]-4-(3,4,4-trimethyl-2,5-dioxoimidazolin-1-yl)butyric acid t-butyl ester To a solution of the title F compound, (2R)-[t-butyloxycarbonyl(4'-chlorobiphenyl-4-sulfonyl)amino]-4-iodobutyric acid t-butyl ester (0.6 g, 0.94 mmol) in 10 mL DMF is added 3,4,4-trimethyl-2,5-dioxoimidazoline and potassium carbonate (0.65 g, 4.72 mmol) followed by 2 mg of 18-crown-6. The reaction mixture is stirred at room RT for 3 h, then partitioned between water and EtOAc. The organic solution is washed with brine, dried over anhydrous Na$_2$SO$_4$ and concentrated. Chomatography on silica gel (eluant; 1/19—EtOAc/hexane) affords the title compound as a white foam (0.25 g, 41%).

H. (2R)-(4'-Chlorobiphenyl-4-sulfonylamino)-4-(3,4,4-trimethyl-2,5-dioxoimidazolin-1-yl)butyric acid The title compound is obtained as a white solid analogously as described in Example 1: m.p. 43° C.; IR 1762, 1737, 1700, 1157; ESI-MS 495 (M$^+$+1), 493 (M$^-$−1).

The title compound is obtained as a white solid analogously as described in Example 56: IR 1735, 1708, 1648, 1155; ESI-MS 526 (M$^-$−1).

EXAMPLE 59

(2R)-(4'-Chlorobiphenyl-4-sulfonylamino)-4-(1,3-dioxo-1,3-dihydroisoindol-2-yl)butyric acid

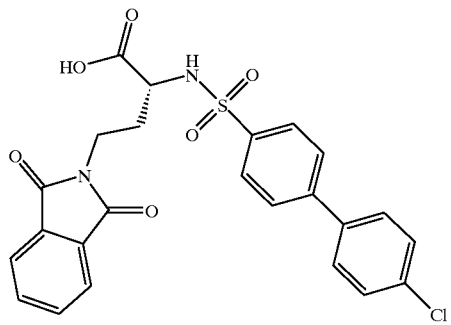

The title compound is obtained as a white solid analogously as described in Example 56: m.p. 205° C. (dec); ESI-MS 497 (M$^-$−1).

EXAMPLE 60

3-Methyl-(2R)-[4-(thiophen-3-yl)benzenesulfonylamino]butyric acid

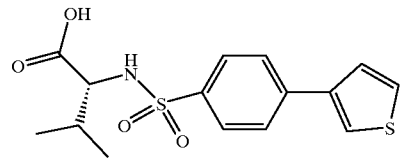

A. 3-Methyl-(2R)-[4-(thiophen-3-yl)benzenesulfonylamino]butyric acid methyl ester

EXAMPLE 57

(2R)-(4'-Chlorobiphenyl-4-sulfonylamino)-4-[(1,3-dioxo-1,5,10,(10aS)-tetrahydroimidazo-[1,5-b]isoquinolin-2-yl)]butyric acid

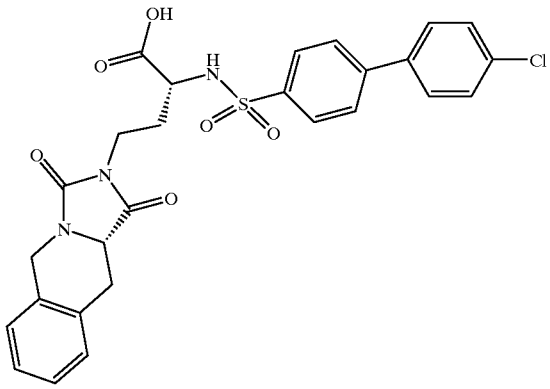

The title compound is obtained as a white solid analogously as described in Example 56: m.p. 70° C.; IR 1764, 1706,1162; ESI-MS 553 (M$^-$−1).

1,3-Dioxo-1,5,10, (10aS)-tetrahydroimidazo-[1,5-b]isoquinoline is prepared as described in J. Pharm. Sci., 67, 718 (1978).

EXAMPLE 58

(2R)-(4'-Chlorobiphenyl-4-sulfonylamino)-4-(1,2,3,4-tetrahydro-1-methyl-2,4-dioxoquinazolin-3-yl)butyric acid

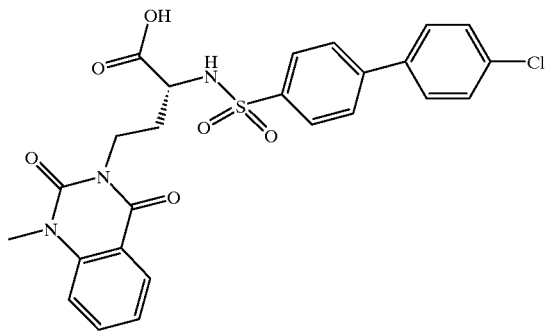

A mixture of (2R)-(4-bromobenzenesulfonylamino) butyric acid methyl ester (9.911 g, 2.6 mmol), 3-thiopheneboronic acid (1.0 g, 7.81 mmol), [1,1'-bis(diphenylphosphino)ferrocene]-dichloropalladium(II) complex with dichloromethane (1:1) (0.117 g, 0.14 mmol) and tribasic potassium phoshate (2.21 g, 10.4 mmol) in 20 mL of dimethoxyethane is heated at reflux for 16 h. The reaction is cooled and concentrated, and the residue is suspended in 100 mL of dichloromethane. The insolubles are removed by filtration and the filtrate is concentrated. Chromatography on silica gel (eluant; 1/9—EtOAc/hexane) affords 0.63 g (68%) of 3-methyl-(2R)-[4-(thiophen-3-yl)benzenesulfonylamino] butyric acid methyl ester.

B. 3-Methyl-(2R)-[4-(thiophen-3-yl)benzenesulfonylamino]butyric acid

The title compound is obtained as a white solid analogously as described in Example 8: m.p. 169° C.; ESI-MS 368 (M$^-$−1).

EXAMPLE 61

5-(1,3-Dioxo-1,3-dihydroisoindol-2-yl)-(2R)-(4'-methoxybiphenyl-4-sulfonylamino)pentanoic acid

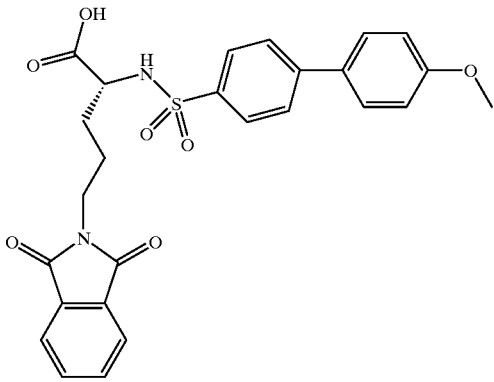

The starting material can be prepared analogously as described in Example 60. The title compound is obtained as described in Example 1.

EXAMPLE 62

(2R)-(4'-Chlorobiphenyl-4-sulfonylamino)-4-(1,3-dioxo-1,3-dihydroisoindol-2-yl)butyric acid hydroxyamide

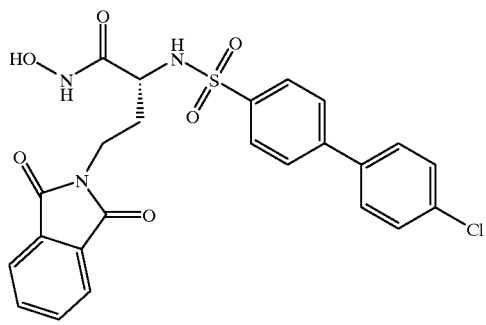

The title compound is obtained as a white solid analogously as described in Examples 2 and 56: m.p. 184–186° C.; ESI-MS 512 (M$^-$–1).

EXAMPLE 63

(2R)-(4'-Chlorobiphenyl-4-sulfonylamino)-4-(3,4,4-trimethyl-2,5-dioxoimidazolin-1-yl)butyric acid hydroxyamide

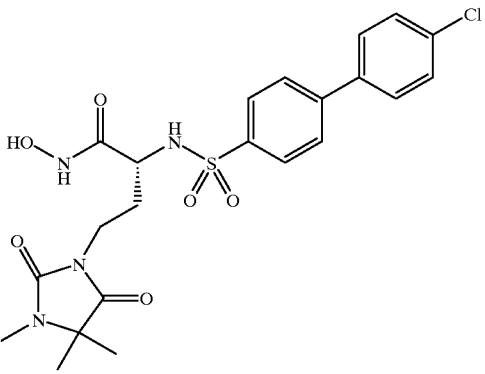

The title compound is obtained as a white solid analogously as described in Examples 2 and 56: m.p. 117–120° C.; ESI-MS 508 (M$^-$–1).

EXAMPLE 64

(2R,S)-(4'-Chlorobiphenyl-4-sulfonylamino)-3-(3,4,4-trimethyl-2,5-dioxoimidazolin-1-yl)propanoic acid

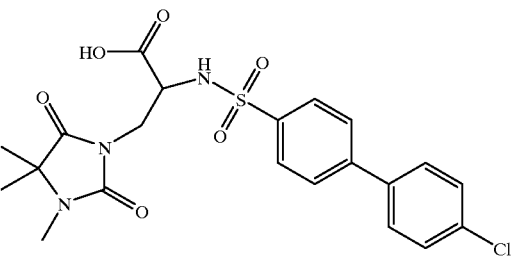

A. Benzhydrylideneaminoacetic acid t-butyl ester

A solution of glycine t-butyl ester hydrochloride (10 g, 59.65 mmol) in 250 mL of dichloromethane is treated with benzophenoneimine (10.8 g, 59.6 mmol) at RT. After 16 h, the mixture is washed with brine, dried over anhydrous MgSO$_4$ and concentrated to give benzhydrylideneaminoacetic acid t-butyl ester as a white solid (16.1 g, 91%).

B. (2R,S)-Amino-3-(3,4,4-trimethyl-2,5-dioxoimidazolin-1-yl)propanoic acid t-butyl ester A solution of the title A compound, benzhydrylideneaminoacetic acid t-butyl ester (1.36 g, 4.59 mmol) in 15 mL of DMF is added to a suspension of sodium hydride in 5 mL of DMF at RT. After 1 h, 3-bromomethyl-1,5,5-trimethylimidazolidine-2,4-dione (1.08 g, 4.59 mmol; prepared according to a known procedure as described in U.S. Pat. No. 1,337,269) is added in one portion and the reaction is heated at 60° C. for 16 h. The mixture is partitioned between EtOAc and water, and the organic solution is washed with water and brine, dried over anhydrous MgSO$_4$ and concentrated. The residue is dissolved in 20 mL of acetonitrile and 2 mL of water and treated with p-toluenesulfonic acid monohydrate (1.39 g, 7.33 mmol), and the mixture is stirred at RT for 16 h. The solvent is evaporated and the residue is partitioned between diethyl ether and 1N aqueous HCl. The organic solution is extracted with 1N aqueous HCl and the combined aqueous extracts are made basic to pH=12 by addition of solid potassium hydroxide (KOH). The product is taken up in ethyl acetate, dried over anhydrous MgSO$_4$ and concentrated to afford 810 mg (62%) of (2R,S)-amino-3-(3,4,4-trimethyl-2,5-dioxoimidazolin-1-yl)propanoic acid t-butyl ester as a colorless oil.

C. (2R,S)-(4'-Chlorobiphenyl-4-sulfonylamino)-3-(3,4,4-trimethyl-2,5-dioxoimidazolin-1-yl)propanoic acid t-butyl ester A solution of the title B compound, (2R,S)-amino-3-(3,4,4-trimethyl-2,5-dioxoimidazolin-1-yl)propanoic acid t-butyl ester (810 mg, 2.84 mmol) and triethylamine (430 mg, 4.26 mmol) in 15 mL of dichloromethane is treated with 4'-chlorobiphenyl-4-sulfonyl chloride (815 mg, 2.84 mmol) at RT. After 16 h, the reaction mixture is washed with water and the organic solution is dried over anhydrous MgSO$_4$ and concentrated. Chomatography on silica gel (eluant; 1% MeOH in dichloromethane) affords 960 mg (63%) of (2R,S)-(4'-chlorobiphenyl-4-sulfonylamino)-3-(3,4,4-trimethyl-2,5-ioxoimidazolin-1-yl)propanoic acid t-butyl ester.

D. (2R,S)-(4'-Chlorobiphenyl-4-sulfonylamino)-3-(3,4,4-trimethyl-2,5-dioxoimidazolin-1-yl)propanoic acid A solution of the title D compound, (2R,S)-(4'-chlorobiphenyl-4-sulfonylamino)-3-(3,4,4-trimethyl-2,5-dioxoimidazolin-1-yl)propanoic acid t-butyl ester (960 mg, 1.79 mmol) in 20 mL of EtOAc is saturated with hydrogen chloride gas for 15 min. The reaction is sealed and stirred for 16 h at RT. The solvent is evaporated and the residue is triturated from petroleum ether to afford 680 mg (79%) of (2R,S)-(4'-chlorobiphenyl-4-sulfonylamino)-3-(3,4,4-trimethyl-2,5-dioxoimidazolin-1-yl)propanoic acid as a white solid: m.p. 198–201° C.; ESI-MS 478 (M$^-$–1).

EXAMPLE 65

(2R,S)-(4'-Chlorobiphenyl-4-sulfonylamino)-3-(1,3-dioxo-1,3-dihydroisoindol-2-yl)propanoic acid

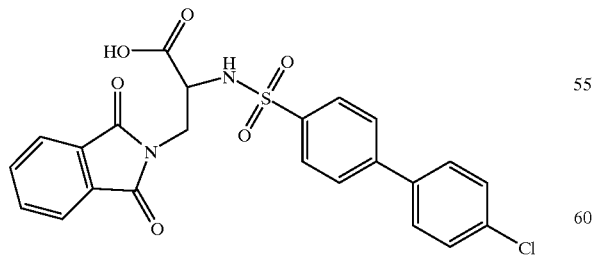

The title compound is obtained as a white solid analogously as described in Example 64: m.p. 262° C. (dec); ESI-MS 483 (M$^-$–1).

EXAMPLE 66

(2R,S)-(4'-Chlorobiphenyl-4-sulfonylamino)-3-(1,2,3,4-tetrahydro-1-methyl-2,4-dioxoquinazolin-3-yl)propanoic acid

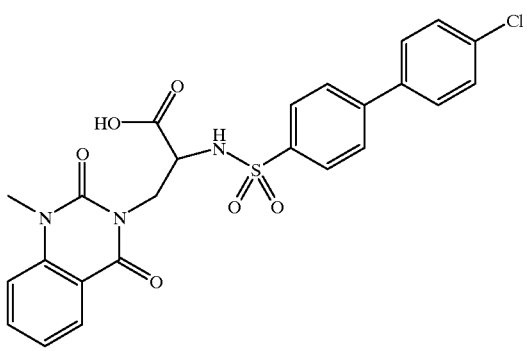

The title compound is obtained as a white solid analogously as described in Example 64: m.p. 218° C. (dec); ESI-MS 512 (M$^-$–1).

3-Bromomethyl-1,2,3,4-tetrahydro-1-methyl-2,4-dioxoquinazoline is prepared as described in U.S. Pat. No. 3,781,288.

EXAMPLE 67

(2R,S)-(4'-Chlorobiphenyl-4-sulfonylamino)-3-(3,4,4-trimethyl-2,5-dioxoimidazolin-1-yl)propanoic acid hydroxyamide

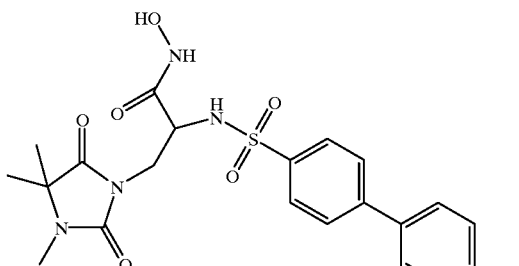

The title compound is obtained as a white solid analogously as described in Examples 2 and 64: m.p. 130° C. (dec); ESI-MS 493 (M$^-$–1).

EXAMPLE 68

(2R)-(4-Phenyloxybenzenesulfonylamino)-4-morpholin-4-yl-4-oxobutyric acid

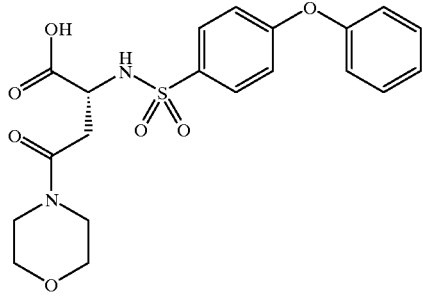

A. (2R)-(t-Butyloxycarbonylamino)-4-morpholin-4-yl-4-oxobutyric acid benzyl ester A solution of D-N-t-butyloxycarbonylaspartic acid benzyl ester (2.53 g, 7.82 mmol) in 30 mL of DMF is treated sequentially with benzotriazol-1-yloxy-tris(dimethylamino)phosphonium hexafluorophosphate (4.15 g, 9.38 mmol), 1-hydroxy-7-azabenzotriazole (1.28 g, 9.38 mmol), diisopropylethylamine (2.5 g, 19.6 mmol) and morpholine (0.82 g, 9.38 mmol). The mixture is stirred at RT for 16 h and is then partitioned between EtOAc and water. The organic solution is washed with water and brine, dried over anhydrous $MgSO_4$ and concentrated. Chomatography on silica gel (eluant; 5% MeOH in dichloromethane) affords 2.91 g (95%) of (2R)-(t-butyloxycarbonylamino)-4-morpholin-4-yl-4-oxobutyric acid benzyl ester as a pale oil.

B. (2R)-Amino-4-morpholin-4-yl-4-oxobutyric acid benzyl ester hydrochloride

A solution of the title A compound, (2R)-(t-butyloxycarbonylamino)-4-morpholin-4-yl-4-oxobutyric acid benzyl ester (2.91 g, 7.42 mmol) in 50 mL of ethyl acetate is saturated with hydrogen chloride gas for 15 min. The reaction is sealed and stirred for 3 h at RT. The solvent is evaporated to afford 2.27 g (93%) of (2R)-amino-4-morpholin-4-yl-4-oxobutyric acid benzyl ester hydrochloride as a white solid.

C. (2R)-(4-Phenyloxybenzenesulfonylamino)-4-morpholin-4-yl-4-oxobutyric acid benzyl ester A solution of the title B compound, (2R)-amino-4-morpholin-4-yl-4-oxobutyric acid benzyl ester hydrochloride (420 mg, 1.28 mmol) in 5 mL of dichloromethane is treated with triethylamine (345 mg, 2.82 mmol) followed by a solution of 4-phenoxybenzenesulfonyl chloride (345 mg, 1.28 mmol) in 2 mL of dichloromethane. The reaction is stirred for 16 h, then partitioned between dichloromethane and water. The organic solution is washed with brine, dried over anhydrous $MgSO_4$ and concentrated. Chomatography on silica gel (eluant; 3% MeOH in dichloromethane) affords 430 mg (64%) of (2R)-(4-phenyloxybenzenesulfonylamino)-4-morpholin-4-yl-4-oxobutyric acid benzyl ester as a white foam.

D. (2R)-(4-Phenyloxybenzenesulfonylamino)-4-morpholin-4-yl-4-oxobutric acid

A mixture of the title C compound, (2R)-(4-phenyloxybenzenesulfonylamino)-4-morpholin-4-yl-4-oxobutyric acid benzyl ester (430 mg, 0.82 mmol) and 10% Pd on carbon (100 mg) in 10 mL of EtOAc is stirred under hydrogen ($H_2$) atmosphere (1 atm) for 2 h. The catalyst is removed by vacuum filtration though celite, and the filtrate is concentrated to afford 330 mg (100%) of (2R)-(4-phenyloxybenzenesulfonylamino)-4-morpholin-4-yl-4-oxobutyric acid as a white solid: m.p. 147–149° C.; ESI-MS 433 ($M^-$–1).

EXAMPLE 69

(2R)-(4'-Chlorobiphenyl-4-sulfonylamino)-4-morpholin-4-yl-4-oxobutyric acid

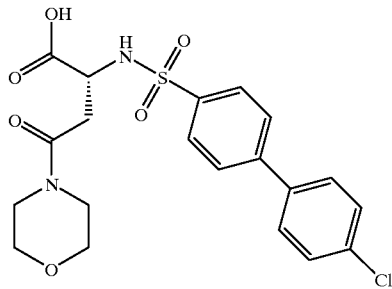

The title compound is obtained as a white solid analogously as described in Example 68: m.p. 144–146° C.; ESI-MS 452 ($M^-$–1).

EXAMPLE 70

(2R)-(4-Phenyloxybenzenesulfonylamino)-4-morpholin-4-yl-4-oxobutyric acid hydroxyamide

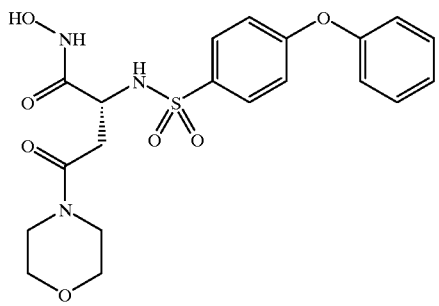

The title compound is obtained as a white solid analogously as described in Examples 2 and 68: m.p. 161–163° C.; ESI-MS 448 ($M^-$–1).

EXAMPLE 71

(2R)-(4'-Chlorobiphenyl-4-sulfonylamino)-4-morpholin-4-yl-4-oxobutyric acid hydroxyamide

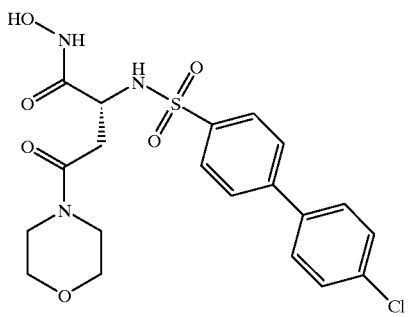

The title compound is obtained as a white solid analogously as described in Examples 2 and 68: m.p. 139–141° C.; ESI-MS 466 (M⁻–1).

EXAMPLE 72

(2S)-(4'-Chlorobiphenyl-4-sulfonylamino)-5-(1,3-dioxo-1,3-dihydroisoinol-2-yl)pentanoic acid

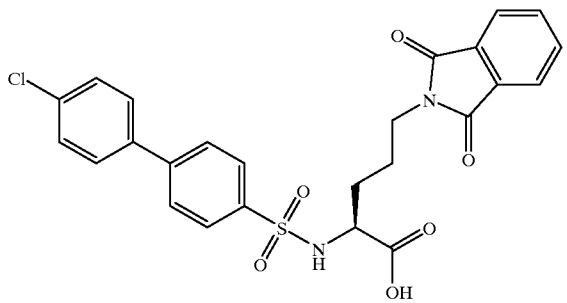

The title compound is obtained as a white solid analogously as described in Example 1: m.p. 175–180° C.; NMR(1:100 CD$_3$OD/CDCl$_3$) 1.66–1.88 (m, 4H), 3.69 (t, 2H, J=6.4), 4.07–4.17 (m, 1H), 5.31 (d, 1H, J=8.8), 7.44 (d, 2H, J=8.6), 7.52 (d, 2H, J=8.6), 7.65 (d, 2H, J=8.4), 7.68–7.73 (m, 2H), 7.79–7.83 (m, 2H), 7.91 (d, 2H, J=8.4); IR 1777, 1702, 1598, 1344, 1170; MS 511 (M⁻–1), 513 (M⁻+1).

EXAMPLE 73

(2R)-(4-Phenoxy-benzenesulfonylamino)-5-(1,1,3-trioxo-2,3-dihydrobenzoisothiazol-2-yl)pentanoic acid

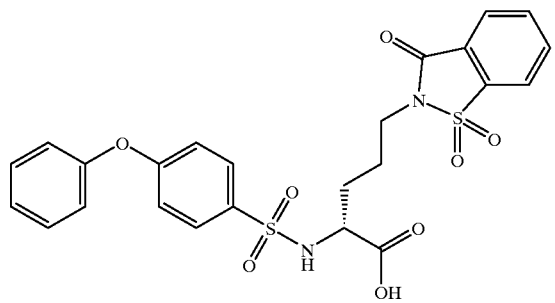

A. (2R)-t-Butoxycarbonylamino-5-(1,1,3-trioxo-2,3-dihydrobenzoisothiazol-2-yl)pentanoic acid t-butyl ester Sodium hydride (0.311 g, 7.78 mmol) was added to a solution of saccharin (1.73 g, 9.44 mmol) and 18-crown-6 (0.025 g) in 10 mL of DMF. After stirring at RT for 30 min, (2R)-(t-butyloxycarbonylamino)-5-iodopentanoic acid t-butyl ester (2.78 g, 6.96 mmol) in 10 mL of DMF was added, and the solution was stirred at RT for 30 min, then at 60° C. for 6 h. The solvent was removed under reduced pressure, and the residue was partitioned between ethyl acetate and 0.05M aqueous HCl. The organic phase was washed with water and brine, dried over MgSO$_4$ and concentrated. The crude material was purified by silica gel chromatography (hexane/ethyl acetate=4/1~3/1) to give the title compound (1.98 g, 63% yield): NMR (400 MHz, CDCl$_3$) 1.44 (s, 9H), 1.46 (s, 9H), 1.68–1.96 (m, 4H), 3.81 (t, 2H, J=7.0 Hz), 4.19–4.29 (m, 1H), 5.09 (br d, 1H, J=7.9 Hz), 7.82–7.93 (m, 3H), 8.06 (d, 1H, J=7.3 Hz).

B. (2R)-Amino-5-(1,1,3-trioxo-2,3-dihydrobenzoisothiazol-2-yl)pentanoic acid t-butyl ester A solution of the title A compound (0.677 g, 1.45 mmol) in 10 mL of methylene chloride was treated with trifluoroacetic acid (TFA) (0.89 mL, 10.0 mmol) at 0° C. After stirring at 0° C. for 30 min, then at RT for 2 h, TFA (0.4 mL) was added to the solution to complete the reaction, then the mixture was stirred at RT for 1.5 h. The solvent was removed under reduced pressure without heating, and the residue was partitioned between ethyl acetate and aqueous sodium bicarbonate. The organic phase was dried over MgSO$_4$ and concentrated to give the title compound (0.494 g, 94% yield): NMR (400 MHz, CDCl$_3$) 1.47 (s, 9H), 1.79–1.99 (m, 4H), 3.62 (t, 1H, J=5.7 Hz), 3.82 (t, 2H, J=6.6 Hz), 7.94–8.01 (m, 2H), 8.06–8.10 (m, 2H).

C. 4-Phenoxybenzenesulfonyl chloride

A solution of chlorosulfonic acid (4.3 mL, 64.6 mmol) in dichloromethane (20 mL) is added dropwise to a solution of diphenyl ether (10 g, 58.8 mmol) in dichloromethane (20 mL) at 0° C. under nitrogen atmosphere. The reaction mixture is slowly warmed up to RT and stirred for 2 h. To the mixture are added oxalyl chloride (6.5 ml, 76.4 mmol) and then DMF (1.5 mL) at RT. After being heated at 40° C. for 1 h, the reaction mixture is stirred at RT for 15 h. The mixture is poured to ice-water and extracted with ether. The organic layer is dried over MgSO$_4$ and evaporated in vacuo to give the title compound quantitatively: NMR (CDCl₃) 7.10 (t, 4H, J=8.6 Hz), 7.22–7.30 (m, 1 H), 7.46 (t, 2H, J=8.6 Hz), 7.98 (d, 2H, J=9.1 Hz).

D. (2R)-(4-Phenoxy-benzenesulfonylamino)-5-(1,1,3-trioxo-2,3-dihydrobenzoisothiazol-2-yl)-pentanoic acid t-butyl ester To a solution of the title compound B (0.500 g, 1.41 mmol) in 15 mL of dioxane and 7.5 mL of water were added triethylamine (0.30 mL, 2.12 mmol), then 4-phenoxybenzenesulfonylchloride (0.492 g, 1.83 mmol) successively at 0° C., and the reaction mixture was allowed to warm to RT. After stirring at RT for 2 h, water and 1M HCl were added to the solution, and the organic material was extracted with ethyl acetate. The organic phase was separated and washed with brine, dried over MgSO₄ and concentrated under reduced pressure. The residue was purified by silica gel chromatography (hexane/ethyl acetate 2/1) to give the title compound (0.571 g, 69% yield): NMR (400 MHz, CDCl₃) 1.29 (s, 9H), 1.68–2.05 (m, 4H), 3.75–3.89 (m, 3H), 5.21 (d, 1H, J=9.0 Hz), 7.00 (d, 2H, J=8.6 Hz), 7.03 (d, 2H, J=7.6 Hz), 7.20–7.26 (m, 1H), 7.40 (t, 2H, J=7.9 Hz), 7.79 (d, 2H, J=9.1 Hz), 7.81–7.94 (m, 3H), 8.06 (d, 1H, J=7.1 Hz).

E. (2R)-(4-Phenoxy-benzenesulfonylamino)-5-(1,1,3-trioxo-2,3-dihydrobenzoisothiazol-2-yl)pentanoic acid The title compound D (0.301 g, 0.513 mmol) was treated with TFA (3.49 mL, 39.5 mmol) at RT and the mixture was stirred at this temperature for 1 h. The solution was concentrated under reduced pressure, then the residue was dissolved in ethyl acetate and water. The organic phase was washed with water and brine, dried over MgSO₄ and concentrated. The product was lyophilized with dioxane to give the title compound (0.300 g, quantitative yield): NMR (400 MHz, CDCl₃) 1.67–1.91 (m, 4H), 3.70–3.76 (m, 2H), 3.88–3.91 (m, 1H), 7.00 (d, 2H, J=9.1 Hz), 7.05 (d, 2H, J=7.6 Hz), 7.21 (t, 1H, J=7.5 Hz), 7.40 (t, 2H, J=8.0 Hz), 7.81 (d, 2H, J=8.8 Hz), 7.91–8.00 (m, 2H), 8.04–8.09 (m, 2H).

EXAMPLE 74

(2R)-[4-(4-Fluoro-phenoxy)-benzenesulfonylamino]-5-(1,1,3-trioxo-2,3-dihydrobenzoisothiazol-2-yl) pentanoic acid

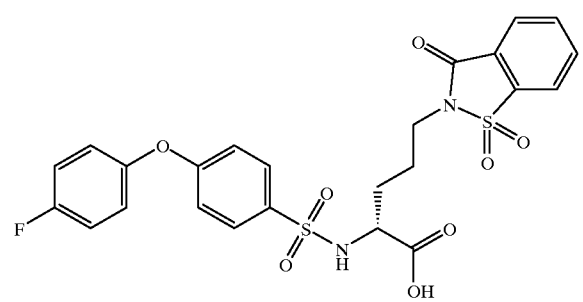

A. 4-(4-Fluorophenoxy)benzenesulfonyl chloride

The title compound is obtained from 4-fluorodiphenyl ether analogously as described under Example 73 C: NMR (CDCl₃) 7.00–7.20 (m, 6H), 7.98 (d, 2H, J=8.6 Hz).

B. (2R)-[4-(4-Fluoro-phenoxy)-benzenesulfonylamino]-5-(1,1,3-trioxo-2,3-dihydrobenzoisothiazol-2-yl)pentanoic acid The title compound is obtained analogously as described in Example 73: NMR (400 MHz, CDCl₃) 1.62–1.93 (m, 4H), 3.70–3.77 (m, 2H), 3.87–3.91 (m, 1H), 7.00 (d, 2H, J=9.1 Hz), 7.06–7.17 (m, 4H), 7.81 (d, 2H, J=8.6 Hz), 7.91–8.00 (m, 2H), 8.07 (t, 2H, J=8.0 Hz).

EXAMPLE 75

(2R)-[4-(4-Fluorophenoxy)benzenesulfonylamino]-5-(1,2,3,4-tetrahydro-1-methyl-2,4-dioxoquinazolin-3-yl)pentanoic acid

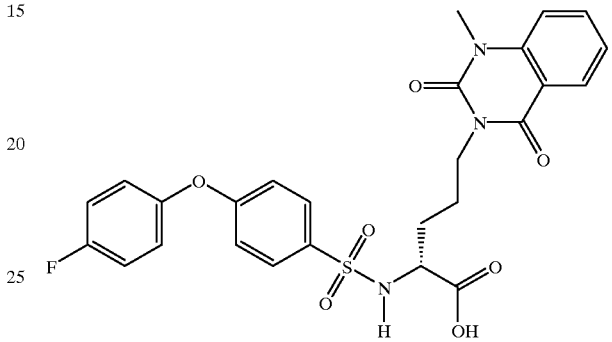

A. (2R)-t-Butoxycarbonylamino-5-(1,2,3,4-tetrahydro-1-methyl-2,4-dioxoquinazolin-3-yl)pentanoic acid t-butyl ester Sodium hydride (0.408 g, 10.2 mmol) was added to a solution of 1,2,3,4-tetrahydro-1-methyl-2,4-dioxoquinazoline (2.17 g, 12.4 mmol) and 18-crown-6 (0.045 g) in 25 mL of DMF. After stirring at RT for 30 min, (2R)-(t-butyloxycarbonylamino)-5-iodopentanoic acid t-butyl ester (3.60 g, 9.02 mmol) in 15 mL of DMF was added, and the solution was stirred at RT for 30 min, then at 60° C. for 6 h. The solvent was removed under reduced pressure, and the residue was partitioned between ethyl acetate and 0.05M aqueous HCl. The organic phase was washed with water and brine, dried over MgSO₄ and concentrated. The crude material was purified by silica gel chromatography (hexane/ethyl acetate 3/1~2/1) to give the title compound (3.81 g, 95% yield): NMR (400 MHz, CDCl₃) 1.42 (s, 9H), 1.45 (s, 9H), 1.60–1.88 (m, 4H), 3.60 (s, 3H), 4.08–4.21 (m, 3H), 5.06 (br d, 1H, J=8.1 Hz), 7.19–7.31 (m, 2H), 7.68 (dt, 1H, J=7.84, 1.56 Hz), 8.22 (dd, 1H, J=7.88, 1.52 Hz).

B. (2R)-Amino-5-(1,2,3,4-tetrahydro-1-methyl-2,4-dioxoquinazolin-3-yl)-pentanoic acid t-butyl ester A solution of the title compound A (3.81 g, 8.52 mmol) in 20 mL of methylene chloride was treated with TFA (5.09 mL, 57.5 mmol) at 0° C. After stirring at 0° C. to RT for 5 h, the mixture was chilled to 0° C., then neutralized carefully with aqueous NaHCO₃ until pH 7~8. The product was extracted with ethyl acetate for three times and combined organic phase was dried over MgSO₄, concentrated under reduced pressure to give the title compound (2.72 g, 92% yield): NMR (400 MHz, CD₃OD) 1.47 (s, 9H), 1.60–1.81 (m, 4H), 3.40 (t, 1H, J=5.8 Hz), 3.60 (s, 3H), 4.06–4.12 (m, 2H), 7.30 (t, 1H, J=7.5 Hz), 7.43, (d, 1H, J=8.4 Hz), 7.74–7.78 (m, 1H), 8.14 (d, 1H, J=7.8 Hz).

C. (2R)-[4-(4-Fluorophenoxy)benzenesulfonylamino]-5-(1,2,3,4-tetrahydro-1-methyl-2,4-dioxoquinazolin-3-yl)pentanoic acid t-butyl ester To a solution of the title compound B (2.98 g, 8.59 mmol) in 90 mL of dioxane and 45 mL of water were added triethylamine (1.80 mL, 12.9 mmol), then 4-(4-fluorophenoxy)benzenesulfonylchloride (3.20 g, 11.2 mmol) successively at 0° C., and the reaction mixture was allowed to warm to RT. After stirring at RT for 3 h, the mixture was chilled to 0° C. then water and 1M HCl were added. The organic material was extracted with ethyl acetate, and the organic phase was washed with brine, dried over $MgSO_4$ and concentrated under reduced pressure to give the crystalline product which was then triturated with ether, filtered and dried to obtain the title compound (4.65 g, 91% yield): NMR (400 MHz, $CDCl_3$) 1.28 (s, 9H), 1.57–1.90 (m, 4H), 3.61 (s, 3H), 3.83–3.92 (m, 1H), 4.08–4.11 (m, 2H), 5.23 (d, 1H, J=9.4 Hz), 6.95–7.28 (m, 8H), 7.69 (t, 1H, J=7.8 Hz), 7.78 (d, 2H, J=8.7 Hz), 8.22 (d, 1H, J=8.0 Hz).

D. (2R)-[4-(4-Fluorophenoxy)benzenesulfonylamino]-5-(1,2,3,4-tetrahydro-1-methyl-2,4-dioxoquinazolin-3-yl)pentanoic acid The title compound is obtained analogously as described in Example 73 E: NMR (400 MHz, $CDCl_3$) 1.59–1.80 (m, 4H), 3.60 (s, 3H), 3.85–3.87 (m, 1H), 4.03–4.05 (m, 2H), 6.98–7.16 (m, 6H), 7.32 (t, 1H, J=7.3 Hz), 7.43 (d, 1H, J=8.4 Hz), 7.76–7.80 (m, 3H), 8.14 (dd, 1H, J=7.9, 1.4 Hz).

EXAMPLE 76
(2R)-(4-Phenoxybenzenesulfonylamino)-5-(1,2,3,4-tetrahydro-1-methyl-2,4-dioxoquinazolin-3-yl)pentanoic acid

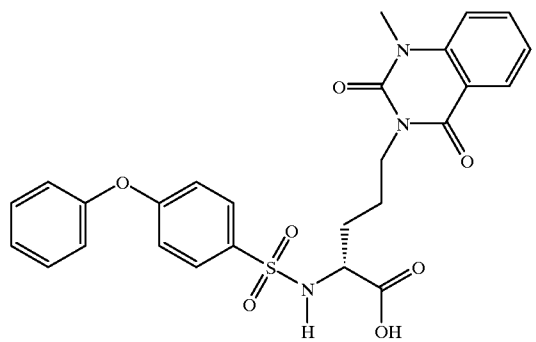

The title compound is obtained analogously as described in Example 75: NMR (400 MHz, $CD_3OD$) 1.59–1.80 (m, 4H), 3.60 (s, 3H), 3.85–3.88 (m, 1H), 4.02–4.07 (m, 2H), 7.00 (d, 2H, J=9.1 Hz), 7.03 (d, 2H, J=8.6 Hz), 7.20 (t, 1H, J=7.6 Hz), 7.30 (t, 1H, J=7.6 Hz), 7.37–7.44 (m, 3H), 7.74–7.79 (m, 1H), 7.79 (d, 2H, J=8.6 Hz), 8.14 (dd, 1H, J=8.1, 1.5 Hz).

The following additional compounds may be prepared using the procedures described above or by modification thereof.

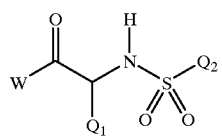

| Example | $Q_1$ | $Q_2$ | W |
|---|---|---|---|
| 77 | —(CH₂)₂—C(O)—N(CH₃)₂ | 4'-Cl-biphenyl-4-yl | —OH, —NHOH |
| 78 | —(CH₂)₂—C(O)—N(CH₃)₂ | 4-(4-methoxyphenoxy)phenyl (4-methylphenyl 4-methoxyphenyl ether) | —OH, —NHOH |
| 79 | —(CH₂)₂—C(O)—N(CH₃)₂ | 4-(3-methoxypropoxy)phenyl substituted aryl | —OH, —NHOH |
| 80 | —(CH₂)₂—C(O)—NH—CH₂CH₂—C₆H₅ | 4'-Cl-biphenyl-4-yl | —OH, —NHOH |

-continued
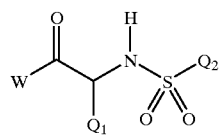
| Example | Q₁ | Q₂ | W |
|---|---|---|---|
| 81 | —(CH₂)₂—C(O)—NH—CH₂CH₂—Ph | 4-MeO-C₆H₄— | —OH, —NHOH |
| 82 | —(CH₂)₂—C(O)—NH—CH₂CH₂—Ph | 4-(n-BuO)-C₆H₄— | —OH, —NHOH |
| 50* | —(CH₂)₂—C(O)—piperidinyl | 4'-Cl-biphenyl-4-yl | —OH, —NHOH |
| 51* | —(CH₂)₂—C(O)—piperidinyl | 4-MeO-C₆H₄— | —OH, —NHOH |
| 52* | —(CH₂)₂—C(O)—piperidinyl | 4-(n-BuO)-C₆H₄— | —OH, —NHOH |
| 64* | —(CH₂)₃—NH—C(O)—(3,4,5-trimethoxyphenyl) | 4'-Cl-biphenyl-4-yl | —OH, —NHOH |
| 53* | —(CH₂)₃—NH—C(O)—(3,4,5-trimethoxyphenyl) | 4-MeO-C₆H₄— | —OH, —NHOH |

-continued

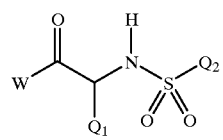

| Example | Q₁ | Q₂ | W |
|---|---|---|---|
| 54* | —(CH₂)₃—NH—C(O)—(3,4,5-trimethoxyphenyl) | 4-(butoxy)phenyl-CH₃ (4-methylphenyl 4-butoxyphenyl ether) | —OH, —NHOH |
| 55* | —(CH₂)₃—NH—C(O)—(3-CF₃-phenyl) | 4'-chloro-biphenyl-4-yl | —OH, —NHOH |
| 56* | —(CH₂)₃—NH—C(O)—(3-CF₃-phenyl) | 4-methoxyphenyl | —OH, —NHOH |
| 57* | —(CH₂)₃—NH—C(O)—(3-CF₃-phenyl) | 4-butoxyphenyl | —OH, —NHOH |
| 58* | —(CH₂)₃—NH—C(O)—(3-F-phenyl) | 4'-chloro-biphenyl-4-yl | —OH, —NHOH |
| 59* | —(CH₂)₃—NH—C(O)—(3-F-phenyl) | 4-methoxyphenyl | —OH, —NHOH |
| 60* | —(CH₂)₃—NH—C(O)—(3-F-phenyl) | 4-butoxyphenyl | —OH, —NHOH |
| 61* | —(CH₂)₃—NH—C(O)—(4-OCF₃-phenyl) | 4'-chloro-biphenyl-4-yl | —OH, —NHOH |

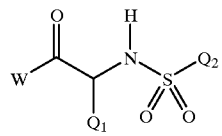

| Example | $Q_1$ | $Q_2$ | W |
|---|---|---|---|
| 62* | —(CH₂)₃-NH-C(O)-C₆H₄-OCF₃ | 4-methylphenyl-O-CH₃ | —OH, —NHOH |
| 63* | —(CH₂)₃-NH-C(O)-C₆H₄-OCF₃ | 4-methylphenyl-O-(CH₂)₃-CH₃ | —OH, —NHOH |

What is claimed is:

1. A compound of formula I

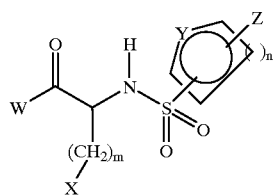

(I)

wherein:

W is —OH or —NHOH;

X is
- a) an unsubstituted or substituted heterocyclic radical, selected from the group consisting of pyrrolidinyl, pyrrolyl, pyrazolyl, oxetanyl, pyrazolinyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidinyl, pyridyl, pyrazinyl, pyridazinyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, benzothiazolyl, benzoxazolyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl, dihydrobenzoisothiazolyl, dihydroquinazolinyl, tetrahydroquinazolinyl and 10 to 15 membered tricyclic ring systems, which have at least one heteroatom in at least one carbon atom-containing ring, in which each ring of the heterocyclic radical containing a heteroatom may have 1, 2 or 3 heteroatoms selected from nitrogen atoms, oxygen atoms and sulfur atoms; with the proviso that when X is a nitrogen containing heterocyclic radical, the heterocyclic radical is attached to the $(CH_2)_m$ moiety by a ring nitrogen and the proviso that nitrogen and sulfur heteroatoms of the heterocyclic radical may also be oxidized;
- b) —NR₁SO₂R₂, in which
    R₁ is hydrogen, alkyl, heterocyclylalkyl, aralkyl or heteroarylalkyl and
    R₂ is hydrogen, alkyl, heterocyclylalkyl, aralkyl, heteroarylalkyl, aryl or heteroaryl;
- c) heterocyclylalkylthio;
- d) —CONR₂R₃, in which
    R₂ and R₃ taken together with the nitrogen atom to which they are attached form a 5- to 7-membered ring, which may optionally contain another heteroatom selected from oxygen, nitrogen and sulfur;

Y is carbon;

z is alkyl, aryl, alkoxy, aryloxy, aralkoxyaryl, aralkoxyheteroaryl, heteroaryl, heterocyclyl, heteroaryloxy, —CONR₂R₃, —NR₁COR₂, —NR₁CONR₂R₃, —OCONR₂R₃, —NR₁COOR₄, or —SO₂R₂, in which
    R₁ is hydrogen, alkyl, heterocyclylalkyl, aralkyl or heteroarylalkyl and
    R₂ and R₃ are independently hydrogen, alkyl, heterocyclylalkyl, aralkyl, heteroarylalkyl, aryl or heteroaryl; or R₂ and R₃ taken together with the nitrogen atom to which they are attached form a 5- to 7-membered ring, which may optionally contain another heteroatom selected from oxygen, nitrogen and sulfur;

R₄ is alkyl, heterocyclylalkyl, aralkyl, aryl or heteroaryl;

m represents an integer from one to six; and n represents the integer two;

or a pharmaceutically acceptable salt thereof.

2. A compound of formula I according to claim 1 wherein

W is —OH or —NHOH; and

X is an unsubstituted or substituted heterocyclic radical, selected from the group consisting or pyrrolidinyl, oxetanyl, pyrazolinyl, imidazolinyl, imidazolidinyl, oxazolidinyl, isoxazolinyl, thiadiazolyl, thiazolidinyl, isothiazolyl, isothiazolidinyl, furyl, tetrahydrofuryl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidinyl, pyrazinyl, pyridazinyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, quinuclidinyl, quinolinyl, tetrahydro-isoquinolinyl, isoquinolinyl, benzopyranyl, indolizinyl, benzofuryl, chromonyl, coumarinyl, benzopyranyl, cinnolinyl, quinoxalinyl, indazolyl, pyrrolopyridyl, furopyridinyl, dihydrobenzoisothiazolyl, dihydroquinazolinyl, tetrahydroquinazolinyl and 10 to 15 membered tricyclic ring systems, which have at least one heteroatom in at least one carbon atom-containing ring, in which each ring of the heterocyclic radical containing a heteroatom may have 1, 2 or 3 heteroatoms selected from nitrogen atoms, oxygen atoms and sulfur atoms;

or a pharmaceutically acceptable salt thereof.

3. A compound of formula I according to claim 1 wherein

X is an unsubstituted or substituted heterocyclic radical, selected from the group consisting of pyrazolyl, oxetanyl, pyrazolinyl, imidazolinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, oxadiazolyl, piperazinyl, 2-oxopiperazinyl, 2-oxopiperidinyl, 2-oxoazepinyl, pyridyl, pyrazinyl, pyridazinyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, benzothiazolyl, benzoxazolyl, quinuclidinyl, quinolinyl, tetrahydroisoquinolinyl, isoquinolinyl, benzopyranyl, benzofuryl, chromonyl, coumarinyl, benzopyranyl, cinnolinyl, quinoxalinyl, indazolyl, pyrrolopyridyl, furopyridinyl, dihydrobenzoisothiazolyl, dihydroquinazolinyl, tetrahydroquinazolinyl and 10 to 15 membered tricyclic ring systems, which have at least one heteroatom in at least one carbon atom-containing ring, in which each ring of the heterocyclic radical containing a heteroatom may have 1, 2 or 3 heteroatoms selected from nitrogen atoms, oxygen atoms and sulfur atoms;

or a pharmaceutically acceptable salt thereof.

4. A compound of formula I according to claim 1 wherein

W is —OH or —NHOH;

X is a nitrogen containing heterocyclic radical;

Y is carbon n is two;

Z is aryl, aryloxy, heteroaryl or heteroaryloxy; and m represents an integer from two to four;

or a pharmaceutically acceptable salt thereof.

5. A compound of formula I according to claim 1 wherein

W is —OH or —NHOH;

X is 1,2,3,4-tetrahydro-1-methyl-2,4-dioxo-quinazolinyl, 3,4,4-trimethyl-2,5-dioxoimidazolinyl, 4-methylbenzenesulfonylamino or 1,1,3-trioxo-2,3-dihydrobenzoisothiazolyl;

Z is aryl, aryloxy, heteroaryl or heteroaryloxy;

Y is carbon, n is two; and m represents an integer from two to four;

or a pharmaceutically acceptable salt thereof.

6. A compound of formula I according to claim 1 wherein

W is —OH;

X is 1,2,3,4-tetrahydro-1-methyl-2,4-dioxo-quinazolinyl or 1,1,3-trioxo-2,3-dihydrobenzoisothiazolyl;

Y is carbon;

n is two;

Z is aryl or aryloxy, whereby in each case aryl is unsubstituted or substituted by halogen; and m represents an integer from two to four;

or a pharmaceutically acceptable salt thereof.

7. A compound of formula I according to claim 1 wherein

W is —OH;

or a pharmaceutically acceptable salt thereof.

8. A compound of formula I according to claim 1 wherein

W is —OH or —NHOH;

X is —$CONR_2R_3$, in which $R_2$ and $R_3$ taken together with the nitrogen atom to which they are attached form a 5- to 7-membered ring, which optionally contains oxygen as another heteroatom;

Y is carbon;

n is two;

Z is aryl or aryloxy; and m represents an integer from one to two;

or a pharmaceutically acceptable salt thereof.

9. A compound of formula I according to claim 1 wherein

W is —OH or —NHOH;

X is —$NR_1COR_2$, in which $R_1$ is hydrogen and $R_2$ is aralkyl or aryl;

Y is carbon;

n is two;

Z is alkoxy or aryl; and m represents an integer from three to four;

or a pharmaceutically acceptable salt thereof.

10. A compound of formula I according to claim 1 wherein

W is —OH or —NHOH;

X is —$NR_1SO_2R_2$, in which $R_1$ is hydrogen and $R_2$ is alkyl, heterocyclylalkyl, aralkyl, heteroarylalkyl, aryl or heteroaryl;

Y is carbon;

n is two;

Z is alkoxy or aryl; and m represents an integer from three to four;

or a pharmaceutically acceptable salt thereof.

11. A compound of claim 1 which is:

(2R)-(4-Phenoxybenzenesulfonylamino)-5-(1,2,3,4-tetrahydro-1-methyl-2,4-dioxoquinazolin-3-yl) pentanoic acid;

(2R)-[4-(4-Fluorophenoxy)benzenesulfonylamino]-5-(1,2,3,4-tetrahydro-1-methyl-2,4-dioxoquinazolin-3-yl) pentanoic acid;

(2R)-[4-(4-Fluorophenoxy)-benzenesulfonylamino]-5-(1,1,3-trioxo-2,3-dihydrobenzoisothiazol-2-yl)pentanoic acid;

(2R)-(4-Phenoxybenzenesulfonylamino)-5-(1,1,3-trioxo-2,3-dihydrobenzoisothiazol-2-yl)pentanoic acid;

or a pharmaceutically acceptable salt of any said compound.

12. A compound of claim 1 which is:

(2R)-(4'-Chlorobiphenyl-4-sulfonylamino)-5-(1,1,3-trioxo-2,3-dihydrobenzoisothiazol-2-yl)pentanoic acid or a pharmaceutically acceptable salt thereof.

13. A pharmaceutical composition comprising an effective matrix-degrading metalloproteinase inhibiting amount of a compound of the formula I according to claim 1 in combination with one or more pharmaceutically acceptable carriers.

14. A pharmaceutical composition for treatment of tumours in warm-blooded animals, comprising an antitumourally effective dose of a compound of the formula I according to claim 1 or a pharmaceutically acceptable salt of such a compound together with a pharmaceutical carrier.

15. A method of inhibiting matrix-degrading metalloproteinase activity in mammals which comprises administering to a mammal in need thereof an effective matrix-degrading metalloproteinase inhibiting amount of a compound of the formula I according to claim 1.

16. A method of inhibiting stromelysin or collagenase activity in mammals which comprises administering to a mammal in need thereof an effective stromelysin or collagenase inhibiting amount of a compound of the formula I according to claim 1.

17. A method of treating matrix-degrading metalloproteinase dependent conditions in mammals which comprises administering to a mammal in need thereof an effective matrix-degrading metalloproteinase inhibiting amount of a compound of the formula I according to claim 1.

18. A method of treatment of warm-blooded animals, in which an antitumourally effective dose of a compound of the formula I according to claim 1 or of a pharmaceutically acceptable salt of such a compound is administered to such a warm-blooded animal suffering from a tumour disease.

19. A process for the preparation of a sulfonylamino acid or sulfonylamino hydroxamic acid of formula I

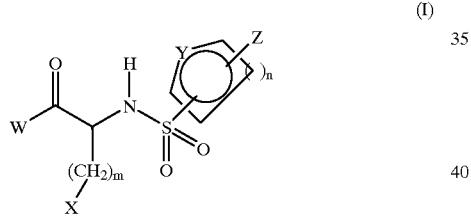
(I)

wherein

W is —OH or —NHOH;

X is
an unsubstituted or substituted heterocyclic radical, selected from the group consisting of pyrrolidinyl, pyrrolyl, pyrazolyl, oxetanyl, pyrazolinyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidinyl, pyridyl, pyrazinyl, pyridazinyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, benzothiazolyl, benzoxazolyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl, dihydrobenzoisothiazolyl, dihydroquinazolinyl, tetrahydro-quinazolinyl and 10 to 15 membered tricyclic ring systems, which have at least one heteroatom in at least one carbon atom-containing ring, in which each ring of the heterocyclic radical containing a heteroatom may have 1, 2 or 3 heteroatoms selected from nitrogen atoms, oxygen atoms and sulfur atoms;

with the proviso that when X is a nitrogen containing heterocyclic radical, the heterocyclic radical is attached to the $(CH_2)_m$ moiety by a ring nitrogen and the proviso that nitrogen and sulfur heteroatoms of the heterocyclic radical may also be oxidized; or heterocyclylalkylthio;

Y is carbon;

Z is alkyl, aryl, alkoxy, aryloxy, aralkoxyaryl, aralkoxyheteroaryl, heteroaryl, heterocyclyl, heteroaryloxy, —$CONR_2R_3$, —$NR_1COR_2$, —$NR_1CONR_2R_3$, —$OCONR_2R_3$, —$NR_1COOR_4$, or —$SO_2R_2$, in which $R_1$ is hydrogen, alkyl, heterocyclylalkyl, aralkyl or heteroarylalkyl and $R_2$ and $R_3$ are independently hydrogen, alkyl, heterocyclylalkyl, aralkyl, heteroarylalkyl, aryl or heteroaryl; or $R_2$ and $R_3$ taken together with the nitrogen atom to which they are attached form a 5- to 7-membered ring, which may optionally contain another heteroatom selected from oxygen, nitrogen and sulfur;

$R_4$ is alkyl, heterocyclylalkyl, aralkyl, aryl or heteroaryl;

m represents an integer from one to six;

n represents the integer one or two;

or a salt thereof, which comprises reacting a compound of formula IV

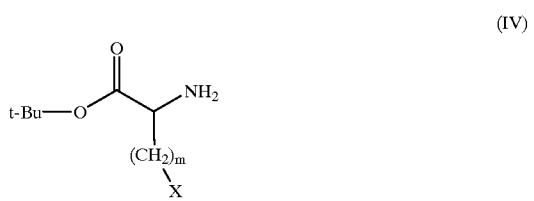
(IV)

in which X is as defined above for compounds of the formula I with a sulfonyl chloride of formula V

(V)

to form a compound of formula VI,

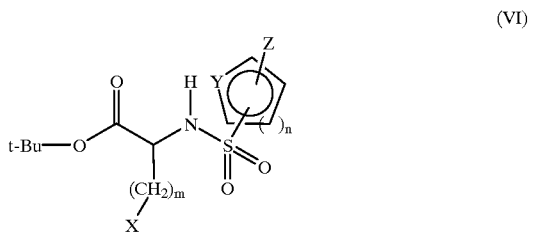
(VI)

and optionally, after treating a compound of formula VI with anhydrous acid to form a compound of formula I where W is a hydroxyl, reacting the compound of formula I where W is hydroxyl with a protected hydroxylamine and removing the protecting group to form a compound of formula I where W is hydroxylamino.

20. A method of selectively inhibiting MT1-MMP activity in mammals which comprises administering to a mammal in need thereof an effective MT1-MMP inhibiting amount of a compound of the formula I according to claim 1.

21. A pharmaceutical composition according to claim 14 wherein the warm-blooded animals are humans.

22. A method according to claim 18 wherein the warm-blooded animals are humans.

23. A compound of formula I according to claim 1 which is:

(2R)-(4'-Chlorobiphenyl-4-sulfonylamino)-5-(1,1,3-trioxo-2,3-dihydrobenzoisothiazol-2-yl)pentanoic acid;

(2R)-(4'-Chlorobiphenyl-4-sulfonylamino)-5-(1,2,3,4-tetrahydro-1-methyl-2,4-dioxo-quinazolin-3-yl)pentanoic acid;

(2R)-(4-Biphenylsulfonylamino)-5-(1,2,3,4-tetrahydro-1-methyl-2,4-dioxoquinazolin-3-yl)pentanoic acid;

(2R)-(4'-chlorobiphenyl-4-sulfonylamino)-5-(3,4,4,-trimethyl-2,5-dioxoimidazolidin-1-yl) pentanoic acid;

(2R)-(4'-Chlorobiphenyl-4-sulfonylamino)-5-(4-methylbenzenesulfonylamino)pentanoic acid;

(2R)-[4-(Pyridin-4-yloxy)benzenesulfonylamino]-5-(1,1,3-trioxo-2,3-dihydrobenzoisothiazol-2-yl)pentanoic acid;

(2R)-[4-(4-Imidazol-1-ylphenoxy)benzenesulfonylamino]-5-(1,1,3-trioxo-2,3-dihydrobenzoisothiazol-2-yl)pentanoic acid;

(2R)-[4-(4-Chlorophenyloxy)benzenesulfonylamino]-5-(1,1,3-trioxo-2,3-dihydrobenzoisothiazol-2-yl) pentanoic acid;

(2R)-(4-Methylpiperazin-1-ylbenzenesulfonylamino)-5-(1,1,3-trioxo-2,3-dihydrobenzoisothiazol-2-yl) pentanoic acid;

(2R)-[4-(4-Methoxybenzoylamino)benzenesulfonylamino]-5-(1,1,3-trioxo-2,3-dihydrobenzoisothiazol-2-yl)pentanoic acid;

(2R)-[4-(4-Phenylpiperidin-1-yl)benzenesulfonyamino]-5-(1,1,3-trioxo-2,3-dihydrobenzoisothiazol-2-yl) pentanoic acid;

(2R)-(4'-Chlorobiphenyl-4-sulfonylamino)-3-{[(1,1,3-trioxo-2,3-dihydrobenzoisothiazol-2-yl)methyl]thio}propionic acid;

(2R)-(4'-Chlorobiphenyl-4-sulfonylamino)-5-(1,1,3-trioxo-2,3-dihydrobenzoisothiazol-2-yl)methyl]thio}pentanoic acid;

(2R)-(4'-Chlorobiphenyl-4-sulfonylamino)-5-(1,2,3,4-tetrahydro-1-methyl-2,4-dioxoquinazolin-3-yl)pentanoic acid hydroxyamide;

(2R)-(4-Biphenylsulfonylamino)-5-(1,2,3,4-tetrahydro-1-methyl-2,4-dioxoquinazolin-3-yl)pentanoic acid hydroxyamide;

(2R)-[4-(Pyridin-4-yloxy)benzenesulfonylamino]-5-(1,1,3-trioxo-2,3-dihydrobenzoisothiazol-2-yl)pentanoic acid hydroxyamide;

(2R)-[4-(4-Imidazol-1-ylphenoxy)benzenesulfonylamino]-5-(1,1,3-trioxo-2,3-dihydrobenzoisothiazol-2-yl)pentanoic acid hydroxyamide;

(2R)-[4-(4-Chlorophenyloxy)benzenesulfonylamino]-5-(1,1,3-trioxo-2,3-dihydrobenzoisothiazol-2-yl) pentanoic acid hydroxyamide;

(2R)-[(4-Methylpiperazin-1-ylbenzenesulfonylamino]-5-(1,1,3-trioxo-2,3-dihydrobenzoisothiazol-2-yl) pentanoic acid hydroxyamide;

(2R)-[4-(4-Methoxybenzoylamino)benzenesulfonylamino]-5-(1,1,3-trioxo-2,3-dihydrobenzoisothiazol-2-yl)pentanoic acid hydroxyamide;

(2R)-[4-(4-Phenylpiperdin-1-yl)benzenesulfonyamino]-5-(1,1,3-trioxo-2,3-dihydrobenzoisothiazol-2-yl) pentanoic acid hydroxyamide;

(2R)-(4'-Chlorobiphenyl-4-sulfonylamino)-3-{[(1,1,3-tiroxo-2,3-dihydrobenzoisothiazol-2-yl)methyl]thio}propionic acid hydroxyamide;

(2R,S)-(4'-Chlorobiphenyl-4-sulfonylamino)-6-(1,2,3,4-tetrahydro-1-methyl-2,4-dioxoquinazolin-3-yl) hexanoic acid;

(2R,S)-(4'-chlorobiphenyl-4-sulfonylamino)-6-(4,4-dimethyl-2,5-dioxoimidazolidin-1-yl)hexanoic acid;

(2R,S)-(4'-Chlorobiphenyl-4-sulfonylamino)-6-(1,2,3,4-tetrahydro-1-methyl-2,4-dioxoquinazolin-3-yl) hexanoic acid hydroxyamide;

(2R,S)-(4'-Chlorobiphenyl-4-sulfonylamino)-6-(4,4-dimethyl-2,5-dioxoimidazolidin-1-yl)hexanoic acid hydroxyamide;

(2R)-(4'-Chlorobiphenyl-4-sulfonylamino)-4-(3,4,4-trimethyl-2,5-dioxoimidazolidin-1-yl)-butyric acid;

(2R)-(4'-Chlorobiphenyl-4-sulfonylamino)-4-[(1,3-dioxo-1,5,10,(10aS)-tetrahydroimidazo-[1,5-b]isoquinolin-2-yl)]butyric acid;

(2R)-(4'-Chlorobiphenyl-4-sulfonylamino)-4-(1,2,3,4-tetrahydro-1-methyl-2,4-dioxoquinazolin-3-yl)butyric acid;

(2R)-(4'-Chlorobiphenyl-4-sulfonylamino)-4-(3,4,4-trimethyl-2,5-dioxoimidazolidin-1-yl)-butyric acid hydroxyamide;

(2R,S)-(4'-Chlorobiphenyl-4-sulfonylamino)-3-(3,4,4-trimethyl-2,5-dioxoimidazolidin-1-yl)propanoic acid;

(2R,S)-(4'-Chlorobiphenyl-4-sulfonylamino)-3-(1,2,3,4-tetrahydro-1-methyl-2,4-dioxoquinazolin-3-yl) propanoic acid;

(2R,S)-(4'-Chlorobiphenyl-4-sulfonylamino)-3-(3,4,4,-trimethyl-2,5-dioxoimidazolidin-1-yl)propanoic acid hydroxyamide;

(2R)-(4-Phenyloxybenzenesulfonylamino)-4-morpholin-4-yl-4-oxobutyric acid;

(2R)-(4'-Chlorobiphenyl-4-sulfonylamino)-4-morpholin-4-yl-4-oxobutyric acid;

(2R)-(4-Phenyloxybenzenesulfonylamino)-4-morpholin-4-yl-4-oxobutyric acid hydroxyamide; or (2R)-(4'-Chlorobiphenyl-4-sulfonylamino)-4-morpholin-4-yl-4-oxobutyric acid hydroxyamide; or a pharmaceutically acceptable salt of any said compound.

* * * * *